US009089316B2

(12) United States Patent
Baust et al.

(10) Patent No.: US 9,089,316 B2
(45) Date of Patent: *Jul. 28, 2015

(54) CRYOGENIC MEDICAL SYSTEM

(75) Inventors: John M Baust, Owego, NY (US); John G. Baust, Candor, NY (US); Roy E. Cheeks, Harper's Ferry, WV (US); Melissa K Dobson, Owego, NY (US); Anthony T. Robilotto, Binghamton, NY (US); Kristi K. Snyder, Candor, NY (US); Robert G. Van Buskirk, Apalachin, NY (US)

(73) Assignee: Endocare, Inc., Austin, TX (US)

( * ) Notice: Subject to any disclaimer, the term of this patent is extended or adjusted under 35 U.S.C. 154(b) by 1129 days.

This patent is subject to a terminal disclaimer.

(21) Appl. No.: 13/038,862

(22) Filed: Mar. 2, 2011

(65) Prior Publication Data

US 2012/0059364 A1    Mar. 8, 2012

Related U.S. Application Data

(63) Continuation-in-part of application No. PCT/US2009/062928, filed on Nov. 2, 2009.

(51) Int. Cl.
*A61B 18/02* (2006.01)
*A61B 18/00* (2006.01)

(52) U.S. Cl.
CPC ....... *A61B 18/02* (2013.01); *A61B 2018/00041* (2013.01); *A61B 2018/00357* (2013.01); *A61B 2018/00577* (2013.01);
(Continued)

(58) Field of Classification Search
CPC ...................... A61B 18/02; A61B 2018/00357; A61B 2018/0262; A61B 2018/00994; A61B 2018/0212; A61B 2018/00041; A61B 2018/00577

USPC .................................. 606/20–26; 62/62, 500
See application file for complete search history.

(56) References Cited

U.S. PATENT DOCUMENTS

| | | | |
|---|---|---|---|
| 3,794,039 A | * | 2/1974 | Kollner et al. ................. 606/22 |
| 4,082,096 A | | 4/1978 | Benson |
| 4,377,168 A | | 3/1983 | Rzasa et al. |

(Continued)

FOREIGN PATENT DOCUMENTS

WO      2010028409      3/2010

OTHER PUBLICATIONS

Fladerer et al., "Homogenous nucleation and droplet growth in supersaturated argon vapor: The cryogenic nucleation pulse chamber", Journal of Chemical Physics (2006), vol. 124. 2006 American Institute of Physics. USA.

(Continued)

*Primary Examiner* — Joseph Stoklosa
*Assistant Examiner* — Eunhwa Kim
(74) *Attorney, Agent, or Firm* — Pepper Hamilton LLP

(57) ABSTRACT

A cryogenic medical device for delivery of subcooled liquid cryogen to various configurations of cryoprobes is designed for the treatment of damaged, diseased, cancerous or other unwanted tissues, particularly as utilized for the ablation of cardiac tissue in the treatment of atrial fibrillation. The device is a closed or semi-closed system in which the liquid cryogen is nitrogen contained in both the supply and return stages. The device is capable of generating cryogen to a supercritical state, specifically supercritical nitrogen, and may be utilized in any rapid cooling systems. As designed, the device also integrates endocardial catheters and epicardial probes.

40 Claims, 19 Drawing Sheets

(52) U.S. Cl.
CPC ............... *A61B 2018/00994* (2013.01); *A61B 2018/0212* (2013.01); *A61B 2018/0262* (2013.01)

(56) References Cited

U.S. PATENT DOCUMENTS

| | | | |
|---|---|---|---|
| 4,829,785 | A | 5/1989 | Hersey |
| 5,147,355 | A | 9/1992 | Friedman et al. |
| 5,237,824 | A | 8/1993 | Pawliszyn |
| 5,334,181 | A | 8/1994 | Rubinsky et al. |
| 5,423,807 | A | 6/1995 | Milder |
| 5,452,582 | A | 9/1995 | Longsworth |
| 5,674,218 | A | 10/1997 | Rubinsky et al. |
| 5,733,280 | A | 3/1998 | Avitall |
| 5,746,736 | A | 5/1998 | Tankovich |
| 5,758,505 | A | 6/1998 | Dobak et al. |
| 5,916,212 | A * | 6/1999 | Baust et al. ............ 606/22 |
| 5,951,546 | A | 9/1999 | Lorentzen |
| 6,096,032 | A | 8/2000 | Rowland |
| 6,161,543 | A | 12/2000 | Cox et al. |
| 6,171,301 | B1 | 1/2001 | Nelson et al. |
| 6,306,129 | B1 | 10/2001 | Little et al. |
| 6,468,268 | B1 | 10/2002 | Abboud et al. |
| 6,468,269 | B1 | 10/2002 | Korpan et al. |
| 6,887,234 | B2 | 5/2005 | Abboud et al. |
| 7,160,291 | B2 | 1/2007 | Damasco et al. |
| 7,207,985 | B2 | 4/2007 | Duong et al. |
| 7,303,554 | B2 | 12/2007 | Lalonde et al. |
| 7,306,589 | B2 | 12/2007 | Swanson |
| 7,416,548 | B2 | 8/2008 | Baust et al. |
| 7,416,551 | B2 | 8/2008 | Ad |
| 2001/0021847 | A1 | 9/2001 | Abboud et al. |
| 2003/0055416 | A1 * | 3/2003 | Damasco et al. ............ 606/21 |
| 2004/0215295 | A1 * | 10/2004 | Littrup et al. ............ 607/96 |
| 2005/0090814 | A1 | 4/2005 | Lalonde et al. |
| 2005/0261671 | A1 | 11/2005 | Baust et al. |
| 2005/0261753 | A1 * | 11/2005 | Littrup et al. ............ 607/96 |
| 2006/0079867 | A1 | 4/2006 | Berzak et al. |
| 2006/0129142 | A1 | 6/2006 | Reynolds |
| 2006/0235375 | A1 | 10/2006 | Littrup et al. |
| 2007/0021741 | A1 | 1/2007 | Abboud et al. |
| 2007/0233055 | A1 | 10/2007 | Abboud et al. |
| 2007/0244474 | A1 | 10/2007 | DeLonzor et al. |
| 2007/0277550 | A1 | 12/2007 | Li et al. |
| 2008/0009845 | A1 | 1/2008 | Duong et al. |
| 2008/0027422 | A1 | 1/2008 | Vancelette et al. |
| 2008/0147056 | A1 | 6/2008 | van der Weide et al. |
| 2008/0173028 | A1 | 7/2008 | Littrup et al. |
| 2008/0255551 | A1 | 10/2008 | DeLonzor |
| 2008/0300584 | A1 | 12/2008 | Lentz et al. |
| 2009/0012510 | A1 * | 1/2009 | Bertolero et al. ............ 606/14 |
| 2009/0281533 | A1 | 11/2009 | Ingle et al. |
| 2009/0318913 | A1 | 12/2009 | Li |
| 2010/0057064 | A1 | 3/2010 | Baust et al. |
| 2010/0057067 | A1 | 3/2010 | Baust et al. |
| 2010/0241112 | A1 | 9/2010 | Watson |
| 2011/0152849 | A1 | 6/2011 | Baust et al. |

OTHER PUBLICATIONS

Bartlett, The Fundamentals of Heat Exchangers, Industrial Physicist (2006) 18-21.

Office Action dated Feb. 20, 2013 received in U.S. Appl. No. 12/548,321.

Office Action dated Aug. 14, 2012 received in related U.S. Appl. No. 12/553,005.

Final Office Action dated Jan. 18, 2013 received in related U.S. Appl. No. 12/553,005.

* cited by examiner

FIG. 4

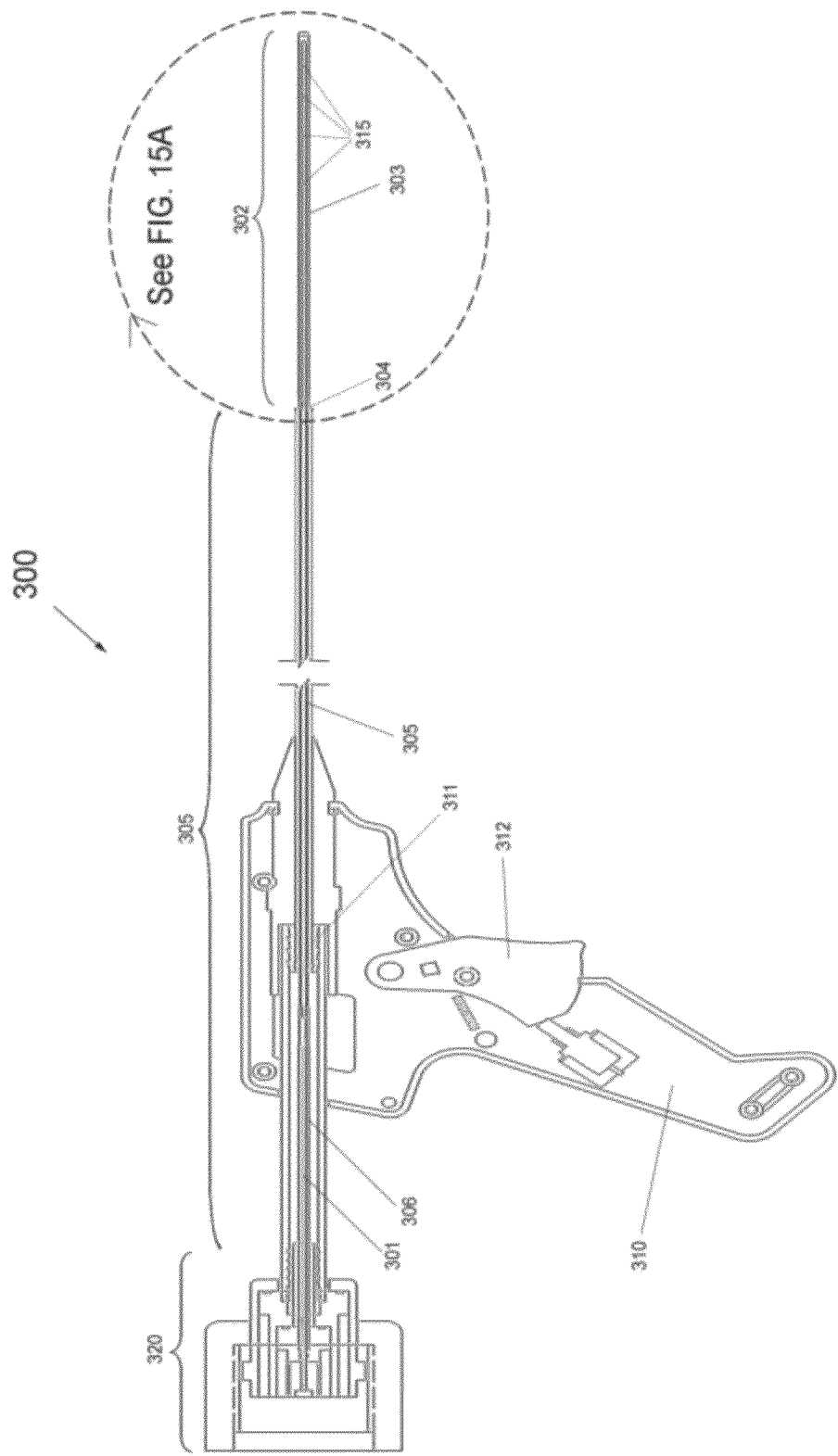

CRYOGENIC MEDICAL SYSTEM

RELATED APPLICATIONS

This is a continuation-in-part application claiming benefit of International PCT Application No. US2009/062928 filed on Nov. 2, 2009 and titled A Cryogenic System and Method of Use under 35 U.S.C. §365(c), which is incorporated herein by reference. The present application is related to U.S. Non-provisional patent application Ser. No. 12/553,005 filed on Sep. 2, 2009, U.S. Provisional Patent Application Ser. No. 61/093,916 filed on Sep. 3, 2008, U.S. Non-provisional patent application Ser. No. 12/562,301 filed on Sep. 18, 2009, and U.S. Provisional Patent Application Ser. No. 61/098,244 filed on Sep. 19, 2008, incorporated herein by reference.

FIELD OF THE INVENTION

The present invention relates generally to the medical technology field and, in particular, to a medical device for use in a cryogenic system as utilized to treat cardiac arrhythmias, such as in atrial fibrillation.

BACKGROUND OF THE INVENTION

Over a recent number of years, there has been a strong movement within the surgical community toward minimally invasive therapies. The main goals of the minimally invasive therapies include: 1) eradication of targeted tissue, 2) decreased hospitalization time, 3) limited postoperative morbidities, 4) shortened return interval to daily functions and work, and 5) reduced overall treatment cost. One minimally invasive method of treating a disease state is through tissue freezing, also known as cryotherapy. Currently, cryotherapy is used to treat numerous disease states including organ confined tumors such as prostate, kidney, liver, as well as cardiovascular disease, retinal detachment, pain management, and other illness/disease states.

Cryotherapy is an effective yet minimally invasive alternative to radical surgery and radiation therapy. The procedure is done under either general or epidural anesthesia. The procedure offers patients a quicker recovery and reduced severity of potential side effects. Without the expense associated with major surgery or an extended hospital stay, cryotherapy is also a cost-effective treatment option.

The approaches utilized to date have focused on the delivery of liquid cryogen through the use of moderate to high pressure on the entire system or piston and bellows compression to drive fluid movement. At present, current systems utilizing liquid nitrogen operate at pressures between 14-480 psi; the systems in use cannot operate or withstand pressures greater that about 500 psi. Further, the use of heat exchangers have been limited to coils placed into a bath of cryogen to allow for time consuming, inefficient passive subcooling of the cryogen in which activation of these devices circulate a cryogen (such as liquid nitrogen) to a probe to create a heat sink, thus resulting in tissue freezing.

There exists a need for improvements in cryotherapy, and medical devices or components associated with the treatment, to better circulate liquid cryogen to a cryoprobe, to provide for rapid delivery through small tubes, and to facilitate improved measures for treatment and cost. The system of the present invention will allow for the circulation (cooling, delivery, and return) of liquid cryogen to a cryoprobe for the freezing of target tissue. The invention will facilitate the eradication of tissue, decrease hospitalization time, limit postoperative morbidities, shorten return to daily functions and work, and further reduce the overall treatment cost. Desirably, these improvements to device design and application will also increase its utilization for the treatment of multiple disease states.

One such category of diseases includes cardiac arrhythmias, a significant health problem. Atrial fibrillation is a common cardiac arrhythmia. Although atrial arrhythmias may not be as fatal as frequently as ventricular arrhythmias, atrial arrhythmias increase risk factors for other conditions such as embolisms. Further, atrial arrhythmias can contribute to the onset of ventricular arrhythmia.

Specifically, atrial fibrillation is a condition that results from the abnormal electrical activity within the heart. This abnormal activity may occur at regions of the heart including the sinoatrial (SA) node, the atrioventricular (AV) node, or within other areas of cardiac tissue. Moreover, atrial fibrillation may be caused by abnormal activity within one or more focal centers within the heart, the electrical activity generally decreasing the efficiency with which the heart pumps blood. It is believed that these foci can originate from within the pulmonary veins of the atrium, particularly the superior pulmonary veins. Therefore, it is also believed that atrial fibrillation can be controlled by structurally altering or ablating the tissue at or near the focal centers of the abnormal electrical activity to form a "conduction block".

In one method, during open-heart surgery, and known as a surgical or epicardial ablation, the tissue of the heart and pulmonary veins is altered by making a series of incisions in a maze-like pattern in the atria and sewn back together (may be referred to as the "Cox maze" procedure). As the incisions heal, scar tissue forms, and the scar tissue may block the conductive pathways thought to cause atrial fibrillation.

Probe devices in the prior art have been designed for use directly in an open chest mode for the creation of linear cryogenic or radiofrequency (RF) lesions applied directly to an exposed heart. Parallel probe members have been used to create lesions through the tissue thickness, one member penetrating the myocardial tissue to the inside of an atrial chamber and cooperate with a member on the outer surface. Other designs have penetrated into the pericardial space using a subxiphoid or thoracic transcutaneous approach. Such probes may be used in conjunction with an endocardial catheter or other stimulation device to treat ventricular tachycardia (VT).

On the otherhand, a less invasive method of structurally altering tissue of the heart and pulmonary veins involves ablating tissue through the use of an ablation catheter, also known as endocardial ablation. The techniques typically are characterized by the application of energy to create lesions at the foci or other areas possessing abnormal electrical activity. Ablation catheters can also be used to create lesions at the heart to block electrical signals or alter a travel path of electrical signals at the heart. One example of an ablation catheter delivers RF energy to ablate tissue. Another example of an ablation catheter delivers cryotherapy to ablate tissue by freezing it.

Cryotherapy may be delivered to an appropriate treatment site inside a patient's heart or circulatory system with a cryotherapy catheter. This method, termed cryoplasty or cryotherapy may be used to cool or otherwise freeze a portion of target tissue to ablate the target tissue. A cryotherapy catheter generally includes a treatment member at its distal end, such as an inflatable balloon having a cooling chamber inside. To deliver the cryotherapy, the inflatable balloon may be introduced at a treatment site inside a patient, and the balloon positioned and then inflated. Once in position, a cryogenic fluid may be provided by a source external to the patient at the proximal end of the cryotherapy catheter, and delivered distally through a lumen to the cooling chamber, where it may be released. Release of the cryogenic fluid into the chamber can cool the chamber (e.g. through the Joule-Thompson effect), and correspondingly, with the balloon's outer surface, which may be in contact with tissue that is to be ablated. Gas resulting from release of the cryogenic fluid may be exhausted proximally through an exhaust lumen to a reservoir or pump external to the patient. As a result of the release of the cryogenic fluid into the chamber and the exhausting of the resulting gas from the chamber, tissue adjacent to the balloon may be cooled to a therapeutic level (e.g. 0° C., −20° C., −60° C., −80° C., or some other appropriate value) for an appropriate period of time.

For example, cryoplasty may be used to cool or freeze, and simultaneously dilate a lesion within a blood vessel that might otherwise lead to restenosis or recoil. Cryotherapy may also be used to create lesions in a heart to treat atrial fibrillation. However, creating lesions in a heart using cryotherapy poses a challenge in the delivering sufficient cooling to create a transmural (i.e., a through thickness) lesion. In addition, blood delivered to and from the heart constantly provides heat to a target site at the heart, thereby counteracting the cooling being delivered by the cryotherapy and limiting the amount of cooling that can be delivered to the target site. This in turn, further prevents a transmural lesion, or lesion of a desired size or characteristic, from being created at the target tissue. Thus, there is currently a need for an improved device and method to perform ablation therapy. The device would address an important aspect of treatment by providing lesions, transmural and continuous in character (otherwise, segmenting the heart and preventing fibrillation would not be possible).

Minimally invasive surgical techniques are known for performing medical procedures within all parts of the cardiovascular system. Exemplary known procedures include the steps of passing a small diameter, highly-flexible catheter through one or more blood vessels and into the heart. When positioned as desired, additional features of the catheter are used, in conjunction with associated equipment, to perform all or a portion of a medical treatment, such as vessel occlusion, tissue biopsy, or tissue ablation, among others. Almost always, these procedures are performed while the heart is beating and blood is flowing. Even though visualization and positioning aids are adequate for general placement of the device, maintaining the device in a selected position and orientation can be difficult as the tissue moves and blood flows, especially during a procedure that must be done quickly. As diagnostic and visualization equipment and techniques continue to evolve, it has become possible to identify tissue areas to be treated with greater precision while quickly situating the device and effectuating treatment.

In addition to the challenges presented by moving tissue and flowing blood, the actual topography of the tissue being treated presents challenges. For example, the interior chambers of the heart have surfaces that are irregular, uneven, and fibrous, as are the openings to the blood vessels. Thus, for procedures that call for uniform tissue contact or tissue contact along an extended line, the structure and techniques for use of known devices can be deficient in some regards. For example, catheter-based devices are known for placement in the left atrium for ablating tissue within the atrium for the purpose of electrically isolating one or more pulmonary veins from the atrium in an attempt to increase the success rate of atrial fibrillation ablation.

Depending on the requirements for a particular procedure, the target tissue that is to be ablated may be characterized as being a single spot, a series of spots or a linear ablation (i.e. a straight line or curvilinear ablation). Due to the nature and the anatomical constraints that are imposed on the procedure by the vasculature, each procedure will present unique issues for consideration. The destruction of tissue by cryoablation requires that the targeted tissue be cooled below a certain temperature. In addition, recent studies have suggested that the cooling rate and subsequent warming rate can affect the percentage of tissue cells destroyed in a cryoablation procedure.

Thus, a need for a cryogenic system is desired that will address the ablation of arrhythmias or tachycardia in atrial or ventricle heart muscles, and more particularly, to an epicardial approach which either addresses the heart directly through an open chest or employs a transcutaneous subxiphoid pericardial approach for the mapping and ablation of tachycardia using laparoscopy or thoracoscopy techniques via an epicardial or intrapericardial approach. There is also a need for a cryogenic system to address such cardiac problems by utilizing an endocardial approach with cryocatheters.

In practice, the standard ablation platform in the treatment of myocardial tissue has been radiofrequency (RF) energy. Radiofrequency energy, however, is not amenable to safely producing circumferential lesions without the potential for serious complications. In particular, while ablating the myocardial cells, heating energy also alters the extracellular matrix proteins, causing the matrix to collapse. This may be the center of pulmonary vein stenosis. Moreover, RF energy is known to damage the lining of the heart, which may account for thromboembolic complications, including stroke. The use of RF energy for ablation can lead to untoward healing responses such as collagen build up at the area of interest after treatment. In some cases, RF ablation may create lesions that cause occlusion of the coronary sinus in post procedure healing. RF also causes significant radiation exposure. A need exists for ablative devices and methods that include improved healing responses.

Although cryotherapy is finding its way into multiple areas of medicine, including cardiac surgery, there are several needs to be addressed from the actual system design, coolant delivery and return, hand-held devices, flexible probe tips and catheters, to interconnected valves, controls, and supplemental support systems. Further, in cardiac settings, the heat sink provided by the blood pool creates a tremendous challenge to current cryoablation approaches as they cannot overcome this heat extraction hurdle. New cryoablation systems, medical devices, and procedures may avoid many of these problems.

SUMMARY OF THE INVENTION

The following invention is a cryogenic medical device designed to deliver subcooled liquid cryogen to various configurations of cryoprobes for the treatment of cardiac tissue, damaged, diseased, and cancerous or other unwanted tissues. The cryogenic medical system addresses the ablation of arrhythmias or tachycardia in atrial or ventricle heart muscles, and more particularly, to epicardial approaches, intrapericardial approaches, and endocardial approaches with cryoprobes or cryocatheters.

The device is a closed or semi-closed system in which supercritical, pseudo-fluidic, or pressurized liquid cryogen is contained in both the supply and return stages.

In one embodiment, the cryogenic medical system is used in patient treatment procedures and comprises: at least one cryoengine (530) including a dewar (501) containing a cryogen, a flow generator (509) within said dewar; at least one pressurization system (503) having one or more heaters (512) arranged therein, at least one port 502, one or more control valves (508, 506, 510, 514), a first vessel (505) and a second vessel (507) interconnected, wherein the first vessel is submersed in the cryogen and has a first temperature and the second vessel is positioned outside the cryogen and has a second temperature greater than the first temperature; at least a first attachment (508) connecting the flow generator to the port of the pressurization system, and one or more cryolines (516) connected to the port; and one or more cryoinstruments (175, 265, 300, 400) comprising one or more tubular structures (301, 306) arranged therein, the cryoinstruments each having a proximal end (121) which connects with the cryolines of the cryoengine and a distal end (65, 68, 138, 302, 404) positioned at a treatment site; wherein the pressurization system produces supercritical cryogen, pressurized cryogen, or one or more pseudo-fluids, alone or in combination.

The cryogenic medical system includes a pressurization system that provides continuous flow of supercritical cryogen to any treatment site, including diseased, cancerous, or undesired tissue, including mammalian cardiac tissue and vessels/vasculature within a mammalian body.

In one embodiment, the cryolines of the cryogenic medical system include supply tubing connecting the cryoengine to the cryoinstrument and supplying the supercritical cryogen to the fine tubular structures of the cryoinstruments. Return tubing allows the cryogen from the distal end of the cryoinstrument to be recycled to the dewar, or cryogen reservoir. The tubular structures within the cryoinstruments, or within any umbilical or connection tubing leading from the cryoengine to the cryoinstruments comprise at least a first tubing and a second tubing positioned in a coaxial or side-by-side configuration. Such design allows for both supply and return of the cryogen within rigid or flexible integral tubing. Various configurations of the cryoengine in combination with cryoinstruments allow the cryogenic medical system to be used to treat a plurality of treatment sites.

The cryogenic medical system freezes mammalian cardiac tissue or any treatment site within about 10 seconds to about 180 seconds. In freezing, an iceball is formed having a diameter of about 2 mm to about 30 mm or greater with a length of about 1 mm to about 130 mm or greater.

In one embodiment, the cryoinstrument takes the form of an epicardial cryogenic probe or an endocardial cryogenic catheter. One embodiment includes a thawing mechanism used in combination with the cryoinstrument. The thawing mechanism may be integral to the cryoinstrument and capable of extending and retracting.

Another embodiment of the cryogenic medical system further comprises one or more connectors that interconnect the cryolines of the cryoengine and the tubular structures of the cryoinstruments. In one aspect, the connectors reversibly attach with and detach from the cryoengine or said cryoinstruments. In another aspect, the connectors also have a telescoping feature, snap-on, twist-on or quick-connect feature providing easy attachment. The telescoping feature extends and retracts to flexibly position the cryolines and the tubular structures.

In another embodiment, the cryogenic medical device integrates a cryoinstrument having a handle which maneuvers the distal end to the treatment site. One aspect of the handle comprises one or more displays which monitor sensors and communicate information for operation of the cryoengine and the cryoprobes.

Further, another embodiment utilizes a cryoinstrument having a telescoping feature which extends and retracts during a treatment procedure. In one embodiment, the supply tubing is interconnected with the return tubing to form an integral cryotube and provide controlled rapid delivery of said supercritical cryogen to and from said distal end of said cryoinstrument. In that aspect, a telescoping feature aligns with the supply and return tubing. The integral cryotube may be rigid or flexible.

In one embodiment of the system, the cryoengine is a multi-port system wherein one or more of the pressurization systems include one or more manifolds to perform multiple treatment procedures. The pressurization systems and the manifolds are configured to perform multiple treatment procedures simultaneously or sequentially. The multiple treatment procedures include one or more epicardial treatments, one or more endocardial treatments, individually or in any combination thereof.

The cryoinstruments in an embodiment also include one or more components that attach to the treatment site. The components clamp a vessel or tissue, such as a mammalian cardiac tissue.

One embodiment of the cryogenic medical system comprises a monitoring system for visualizing placement of the distal end of the cryoinstrument through to the treatment site. A monitoring system may be external to the system or internal to the cryoinstrument, including any fiber optic visualization means. Sensors within the cryoengine and the cryoinstrument monitor conditions including temperature, pressure, leakage, flow rate, cardiac electrical activity, freeze zone formation, computer simulated cryoinstrument configuration, and placement of the cryoinstrument. Further, one embodiment of the system utilizes remote controls within the cryoenginve and/or the cryoinstrument. The remote controls regulate treatment protocols, including treatment times, iceball formation, probe placement, probe angle, probe deflection, temperature and pressure. One aspect of the device uses a warming feature within the cryogenic medical system to maintain a determined size of iceball formation, control treatment times, and allow for probe detachment, tissue thawing, and heating.

One novelty of the system comprises a cryoinstrument which creates a transmural linear lesion.

An embodiment of the present invention is a cryo-apparatus for performing cryoablation in a mammalian heart, the cryo-apparatus comprising: one or more cryoinstruments interconnected with a first cryoline and a second cryoline to form a unitary tubular structure which circulates a cryogenic medium to and from the cryoinstruments; a container having a cryogenic medium contained therein; a heat exchanger surrounded by a subcooling chamber; at least one pressurized apparatus having one or more heaters arranged therein, at least one port, and one or more control valves, wherein at least a first portion of the pressurized apparatus is inside the cryogenic medium and at least a second portion of pressurized apparatus is outside the cryogenic medium; a flow generator which delivers the cryogenic medium to the port of the pressurized apparatus, the control valves releasing the cryogenic medium in a supercritical state from the port to the heat exchanger, and through to said one or more cryoinstruments at a target site of cardiac tissue.

In one embodiment, the cryogen of the invention uses liquid nitrogen as the cryogenic medium, which is pressurized to produce supercritical nitrogen, pseudo-fluidic nitrogen, and/or pressurized liquid nitrogen.

A method of performing cryotherapy on cardiac tissue using the cryogenic medical system comprises: filling the pressurized system with the cryogen; activating the pressurized system to form a pressurized supercritical cryogen; and directing pressurized cryogen through one or more supply lines to the cryoinstruments and from the cryoinstruments through the one or more return lines.

The method may include a step of cryoablating cardiac tissue within the step of directing or as an additional step. In one embodiment, the cryoinstruments utilize flexible interconnections to provide epicardial treatment upon a surface of a mammalian heart or to provide endocardial treatment by way of vessel access or cavity access through to an interior surface of the heart. During the cryoablation, the cryoinstruments create transmural lesions.

Other embodiments of the invention further comprise a step of utilizing hybrid ablation procedures, simultaneously or in tandem, to ablate tissue in any region of the mammalian heart or within vasculature in a mammalian body, alone or in combination with the epicardial and the endocardial treatments. The hybrid ablation procedures comprise cryoablation in combination with surgical intervention or one or more ablative energy sources including radiofrequency, HiFu, and laser therapy. For exemplary purposes, and not limitation, two epicardial probes or two endocardial catheters may be utilized, or one epicardial probe with one endocardial catheter/probe to perform two or more cryo-procedures. Another hybrid procedure may combine an epicardial cryo-procedure with an endocardial cryo-procedure or other ablation approach, including RF, HiFu and/or laser therapy.

Various embodiments and aspects of the cryogenic system can be utilized to treat cardiac arrhythmias, particularly atrial fibrillation. While trying to maintain a liquid coolant or cryogen in the supply path adequately enough and lowering the temperature, a cryogenic supply console is utilized to chill the coolant that is supplied to a desired probe or catheter. While resolving the difficulties associated with placing large consoles at a distance from the operating environments due to associated warming of the liquid coolant, increased fluid resistance (e.g. formation of gas bubbles), and decreased coolant flow to the tip of the probe/catheter, the console is therefore transportable and detachable from the cryogenic source. The interconnected parts and components are also adaptable depending on epicardial (e.g. cryoprobe attachment) or endocardial (e.g. cryocatheter interconnection) treatment options. For example, the console of the invention may integrate treatment options into a hybrid epicardial and endocardial device for the treatment of atrial fibrillation.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion. Further, the below representations of a longitudinal body may not be drawn to scale where particular aspects extend the longitudinal body to lengths up to six feet and beyond (as dependent on the desired application).

FIG. 4 is a top view of one embodiment of a device of the invention.

FIG. 15 is an embodiment of the invention.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1:
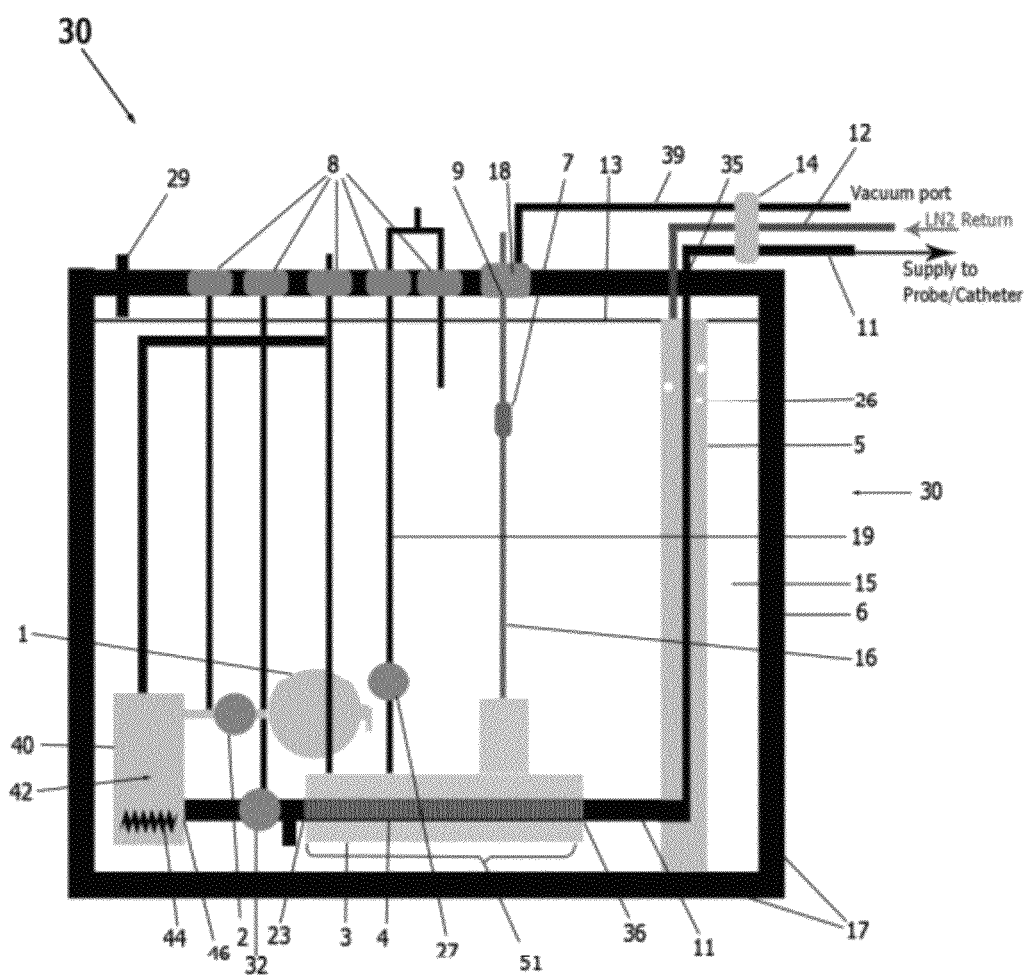
FIG. 1 is a side view of an embodiment of the device of present invention.

An external view of a device and system in accordance with one embodiment of the present invention is shown in FIG. 1. The cryogenic system or device 30 has sidewalls 17 which form a container 6 that encloses an internal cavity, or lumen 15. In an embodiment of FIG. 1, the container 6 takes the form of a vacuum insulated dewar 6. Any size or shape of insulated vessel, however, may be utilized as the dewar 6. The dewar 6 stores liquid cryogen and interconnects a supply line 11 and return line 12 to a probe or catheter (not shown) to form a closed system 30. The dewar 6 may be made of material such as stainless steel, cryo-compatible plastic, or any other material known for providing an insulated vessel. The dewar 6 is filled with liquid nitrogen or other liquefied gas (here, discussing as cryogen) to a maximum level 13. In one aspect, liquid nitrogen may be preferred. In another aspect, any fluidic cryogen may be utilized (e.g. argon, oxygen, helium, hydrogen).

Within the internal cavity, or reservoir 15 of the dewar 6 is a submersible pump 1 which delivers the liquid cryogen to a sealed pressurization apparatus 40. In one embodiment, a valve 2 controls the pressure fill into internal open chamber 42 of the pressurization apparatus 40. Once the cryogen enters the pressurization apparatus 40, an immersion heater 44 housed in the internal open chamber 42 heats the cryogen to create a desired pressure. The liquid nitrogen within the pressurized chamber starts at a temperature of about −196° C. When the heater is activated, it boils the nitrogen within the immediate area. Temperature within internal cavity 42 therefore stays within about −196° C. to −100° C., more typically in the range of about −196° C. to −160° C., or rather between about −170° C. to −160° C. Pressurized cryogen is then released through a valve 32 into the baffled linear heat exchanger 4. In one aspect, liquid nitrogen is converted to supercritical nitrogen (SCN) within the pressurization apparatus. The SCN is then directed to the heat exchanger for subcooling and tuned to the liquid phase to attain an excess temperature. Thereafter, the SCN can be injected into one or more flexible cryoprobes such that the SCN flows with minimal friction to the tip of the probe.

In another aspect, the cryogen can be converted into a pressurized liquid, a pseudo-liquid, or critical cryogen. Other states may include supercritical (pseudo-fluidic) compositions including that of pseudo-liquid and/or pseudo-gas, or any other states, alone or in combination.

In addition to the pump filling the pressurization chamber, other methods could be used including a vacuum pump sucking the liquid nitrogen into the pressurization chamber or the internal cavity could be pressurized and that pressure could drive liquid nitrogen into the chamber. In another aspect, the pump 1 is a propeller, or rather a flow generator 1 to cycle cryogen from the reservoir 15 into the pressurization apparatus 40.

The baffled linear heat exchanger 4 in one embodiment is surrounded by a subcooling chamber 3 which subcools the pressurized cryogen for delivery to external cryoprobes. The subcooling chamber 3 in connection with the heat exchanger 4 at an entrance 23 and an exit opening 36 form an integral unit 51 for supplying subcooled liquid cryogen. From the heat exchanger 4, the subcooled cryogen passes into a supply line 11 and continues out through an exit port 35 and through a control valve 14 where various configurations of cryoprobes are attached. The subcooling chamber may attach a vent line to any of the vents 8, to a supply connecting line 19 controlled through a valve 27, or to a vacuum line 16 through a control valve 7 which is connected to a vacuum pump 18.

The cryogen is returned (as demonstrated by the arrows in FIG. 1) from the cryoprobe via a return tube 12 into a return chamber/cylinder 5 of the dewar 6. The return tube 12 connects into the return cylinder 5 which also surrounds the supply tube 11 that exits the heat exchanger 4. One or more exit ports 35 may be included in a side wall 17 of the dewar 6 or may be a separate unit 14 to incorporate various control valves.

Though the embodiment described in FIG. 1 utilizes a heat exchanger, another embodiment does NOT utilize a heat exchanger. This simplifies the design without sacrificing the SCN state.

In operation, the device 30 is filled through a supply port 29 and then sealed to form a closed system, thereby allowing for the supply, return, collection, and re-utilization of liquid cryogen during its utilization in the medical/surgical field. The entire system 30 may or may not be pressurized during operation. Where the entire system 30 is pressurized during operation, this pressure could facilitate filling the pressure chamber. The system may also be vented to the surrounding environment to prevent excess pressure buildup during operation. In one aspect, the returning cryogen empties into the return cylinder or chamber 5. In another aspect, the returning cryogen may empty as bulk fluid into the internal lumen 15 within the dewar 6.

In one embodiment of the present invention, the linear heat exchanger 4 subcools the liquid cryogen prior to delivery to tissue. In the embodiment of FIG. 1, the linear heat exchanger 4 is an inner chamber 4 which passes through subcooling chamber 3 and is connected via the entrance 23 and exit opening 36. Liquid cryogen passing through the inner chamber 4 is reduced in temperature to a subcooling degree by the outer subcooling chamber 3. The chamber within a chamber configuration includes a subcooling vacuum chamber 3 filled with liquid cryogen upon which a vacuum 18 is drawn through valve-controlled port 9 to reduce the atmospheric pressure on the cryogen. The temperature of the cryogen within the subcooling chamber 3 can then be reduced even further.

Although a heat exchanger is included here, it is noted that a heat exchanger need not be incorporated in a simplified embodiment. The state of SCN is achieved through the use of the use of the pressurization chamber which provides for a continuous controlled delivery of SCN to the treatment site. Having two or more pressurization chambers facilitates the continuous and controlled delivery of the supercritical cryogen, here, SCN.

The subcooling chamber 3 also comprises valve controlled ports 8 external to the maximum liquid cryogen level for monitoring and electronically controlling temperatures, pressures, and flow rates of liquid cryogen passing through the subcooling unit. In one aspect, a vacuum 18 can be drawn on vacuum line 16 at a controlled internal valve 7 or external valve 9. In another aspect, valve controlled ports 8 may be accessible for delivery of liquid cryogen to the subcooling chamber 3 by way of a supply line 19 or as a vent 8 for any excessive gas coming from the subcooling chamber 3. As depicted in FIG. 1, the vacuum 18 also is attached to the cryoprobe(s) by way of vacuum line 39.

Figure 2:
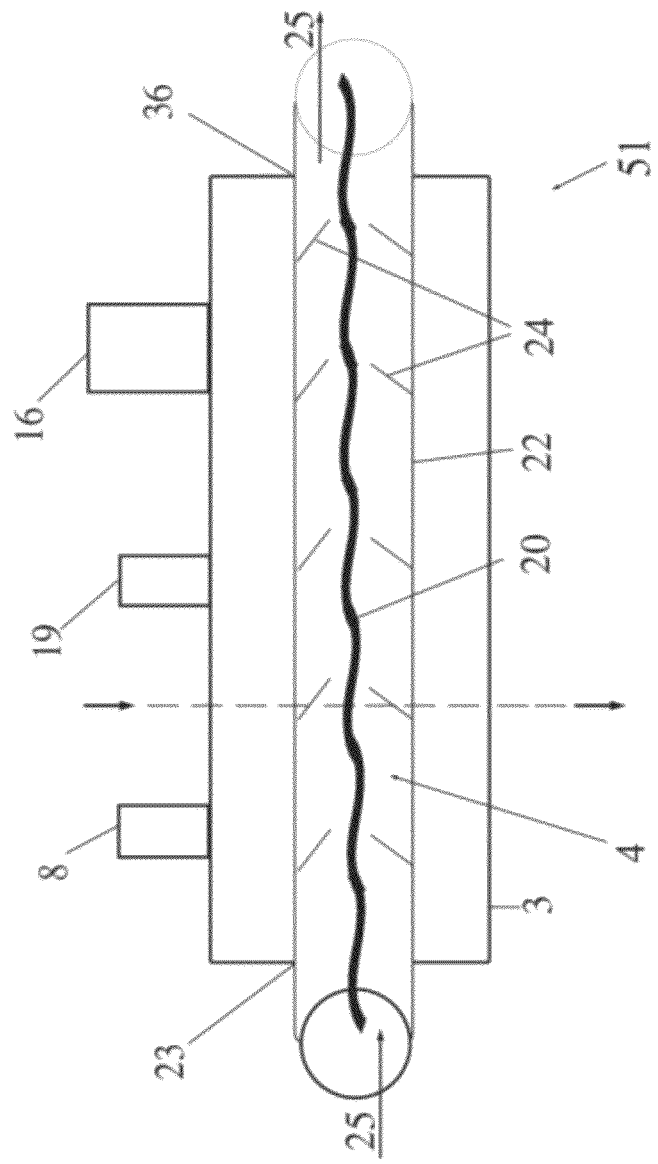
FIG. 2 is a side view of one embodiment of a heat exchanger.
Figure 3:
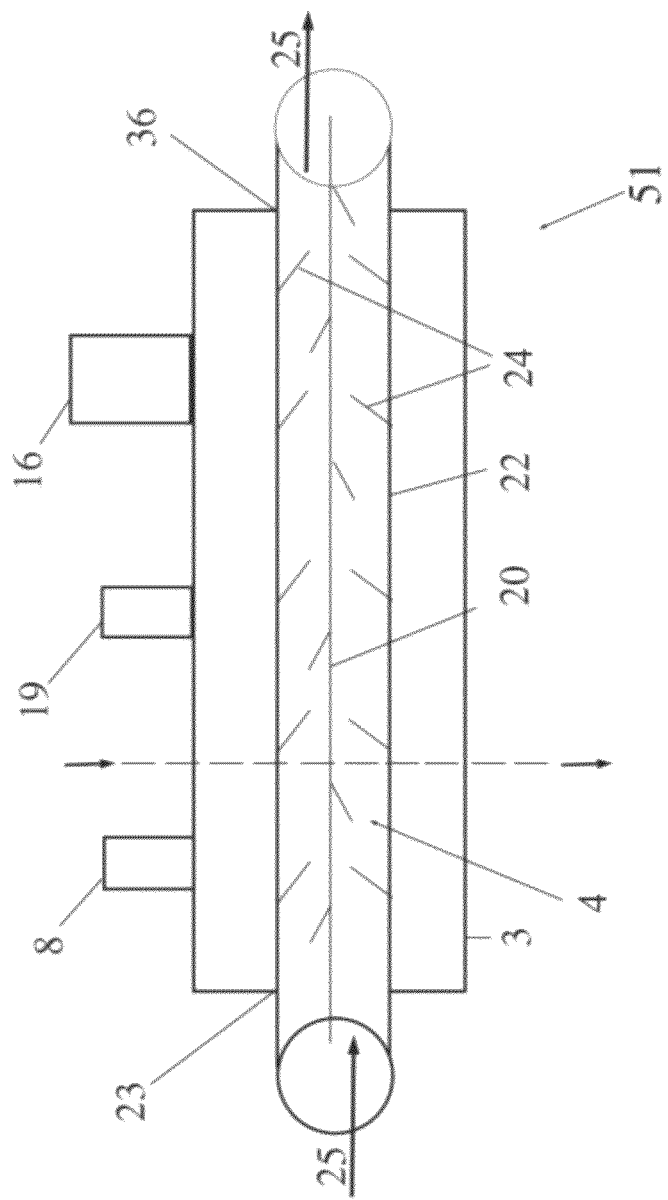
FIG. 3 illustrates a side view of one embodiment of a heat exchanger of the present invention.

Aspects of the linear heat exchanger 4 are illustrated in FIGS. 2 and 3. FIG. 2 and FIG. 3 illustrate side views of different aspects of a linear baffled heat exchanger 4 and subcooling unit 3 as an integral unit 51. An interior central component or spiral 20 within the interior lumen of the chamber 4 operates like a corkscrew to increase the flow path 25 of the liquid cryogen. An outer wall 22 of the inner chamber 4 also comprises baffles 24 which increase the surface area in the heat exchanger for quicker and reduced cooling of the liquid cryogen. As illustrated, a series of baffles 24 emanate into the flow path 25 (as illustrated by arrows) of the cryogen in the inner lumen, thereby increasing the surface area in the heat exchanger 4. The spiral component, however, may be any size and shape as to efficiently increase the flow of liquid cryogen. Planar structures, as described below, or any additional features included to increase surface area may be incorporated or substituted.

FIG. 3 illustrates another embodiment of a linear heat exchanger 4 such that the internal structure 20 has a planar configuration and also operates in a circular motion to increase the flow 25 of the liquid cryogen. An internal structure 20 assists in circulating the flow of liquid cryogen through the interior lumen of the chamber 4, possibly with an interconnected tubular unit that would allow radial movement of the internal structure 20.

One embodiment of the medical device comprises a return chamber 5 which is illustrated as a return cylinder 5 in FIG. 1 such that the return chamber 5 surrounds the supply line 11 coming from the heat exchanger 4. The return chamber 5 and the surrounded supply line may then provide a secondary heat exchanger for the system/medical device 30. Cryogen return is vented into the return chamber 5. In one aspect, the return chamber 5 comprises a series of vent holes 26 near the top of the return chamber 5 to allow for the venting of gas and/or liquid overflow into the main dewar 6. Vent holes 26 allow for the reutilization of cryogen and thus extend the operation time for the medical device 30.

In another aspect, the return tube 12 is vented into the main dewar 6 either directly or by first passing through a linear heat exchanger (similar to the combination of heat exchanger 4 and subcooling chamber 3) to subcool the return cryogen prior to venting into the main dewar 6. Return of the cryogen to the main dewar 6 allows the cryogen to return through a heat exchanger such that the cryogen is reutilized and extends the operation time even longer.

In another embodiment, the medical device 30 may provide a system which is controlled through a series of computer controlled valves including any heaters, sensors, motors, or gauges. The sensors control and monitor pressure, temperature, and fluid level in the dewar, and can measure any metric as may be desired. In one aspect, the sensors monitor pressure levels within defined safety ranges. In another aspect, the sensors may control the pressurization of one or more components internal to the dewar. Any of the valves 2, 7, 8, 9, 27 or 32 including exit portal valve 14, may be automated to enable a controlled and consistent operation of the cryogenic system (e.g. computer controlled operation through the electronically controlled valves).

Figure 4:
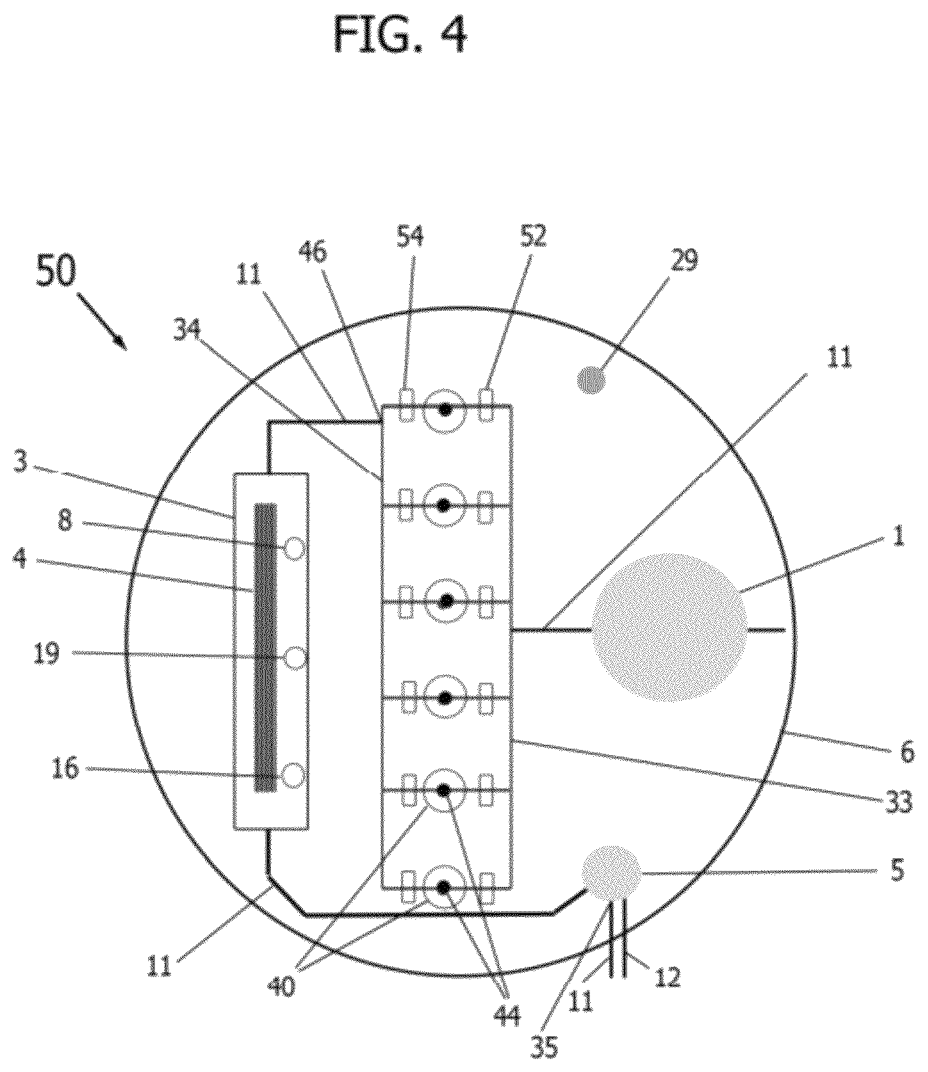

An embodiment of a system 50 is shown in FIG. 4. As illustrated in a top view of the system 50, a series of six pulsatile pressurization chambers 40 are sealed chambers/cylinders 40 within dewar 6 of the closed system 50. From the pump, liquid cryogen in pumped to the pulsatile pressurization chambers 40 which then delivers liquid cryogen in a continuous series of bursts to the heat exchanger 4. The baffled linear heat exchanger 4 provides an enhanced subcooling of the pressurized liquid cryogen while also incorporating an integral subcooling unit 3.

The chambers 40, each comprising an individual immersion heater 44, can then sequentially deliver liquid cryogen at consistent rates, or as specifically determined rates, to the heat exchanger 4.

From the heat exchanger, the subcooled cryogen passes into a supply line 11 and continues out through an exit port 35 where a control valve 14 is positioned and various configurations of cryoprobes are attached. The cryogen is returned (as demonstrated by the arrows in FIG. 4) via a return tube 12 from the cryoprobe to the dewar 6 into a return cylinder 5. The return tube 12 connects into the return cylinder which surrounds the supply tube 11 that exits the heat exchanger 4. The entire system 50 may or may not be pressurized during operation. The device is also vented through vent ports 8 to the surrounding environment to prevent excess pressure buildup during operation.

During the operation of the system 50, as illustrated in the embodiment of FIG. 4, a cryogenic system 50 has been filled and detached from its cryogenic fill tank. In one embodiment, the system 50 is a separate mobile unit protected and contained entirely within an enclosed console for easy access and mobility. Once the system has been sealed, the cryogenic supply can be maintained for several procedures. The reutilization of the liquid cryogen provides a time savings and cost-efficient model for cryotherapeutic and cryosurgical procedures. The system 50 can be further utilized for any process requiring rapid cooling.

In another aspect, however, the system is configured to be run in direct connection to a bulk liquid nitrogen supply.

As depicted, the system 50 comprises a submersible liquid cryogen pump 1 connected to a supply line 11 which directs the liquid cryogen into a supply manifold 33. Here, nitrogen is cryogen utilized. The supply manifold 33 routes the liquid nitrogen into at least one pulsatile pressurization chamber 40 where the liquid cryogen is heated. The pressurized liquid cryogen, here, liquid nitrogen, then starts filling the next pressurization cylinder/chamber 40 in the series such that when one chamber 40 is filling, another can be simultaneously pressurized and prepared for use. This permits a wave of activity through the cylinders so that it can cycle through each step of system operation. As the pressurized cryogen is delivered to the heat exchanger 4, and passes the subcooled pressurized cryogen out through the supply line 11 through the exit port 35 and into the attached cryoprobes, another pressurization chamber is filled and pressurized. The simultaneous use and pressurization of the liquid cryogen provides for the sequential delivery of liquid cryogen in a continuous series of pulsations to a cryogenic instrument or probe. A manifold may be integrated to supply continuous pressure. The heat exchanger may also be utilized to supply continuous delivery of sub-cooled SCN.

In one embodiment, liquid nitrogen is used; however, any cryogenic fluid may be utilized, including nitrogen, argon, helium, hydrogen, and other such desired fluids. Each pressurization apparatus 40 comprises a pressure valve controlled inlet 52, valve controlled outlet 54, and vent ports as may be desired, as well as an immersion heater 44. In one aspect, the filling of the pressurization apparati 40 is controlled through a series of pressure valves 52 on the supply manifold 33. Liquid cryogen is heated within each pressurized apparatus. Pressurized liquid cryogen is then released through the control valve 54 to an outlet port/opening 46 of an outlet manifold 34 to the supply line 11, and delivered to a baffled linear heat exchanger 4. In the illustrated embodiment, a subcooling unit 3 surrounds the heat exchanger 4 for more rapid cooling.

In one embodiment, the cryogenic device 50 comprises six pressurized apparati 40 linked together. Other embodiments, however, may comprise any number of pressurized apparati 40 individually or linked together in combination. The apparati can then be controlled individually or in sequence to deliver pressurized liquid cryogen to the heat exchanger 4. In another aspect, one or more pressurization apparati 40 may be arranged to supply one or more cryoprobes. Further, the series of pressurized apparati 40 may be interconnected with another series of apparati 40.

In the embodiment of FIG. 4, six pulsatile pressurization chambers 40 are housed within a support network of a console. In one example, three of the cylinders within one-half of the dewar simultaneously fill while three cylinders within the other half of the dewar deliver cryogen out through the outlet manifold. (Any number of cylinders, however, may be operated individually or in desirable combinations.) Liquid cryogen is heated in the sealed pressurization chambers 40. Pressure is increased to a specified level in the sealed pressurization chambers 40, and then the pressurized cryogen is controllably released into a heat exchanger 4 to subcool the cryogen. In one aspect, a subcooling vacuum chamber 3 surrounds the heat exchanger 4, facilitating the delivery of subcooled cryogen to an attached cryoprobe (also referred to as probe or catheter). As the pressurized cryogen is utilized, a sensor within the heat exchanger monitors the temperature and pressure of the subcooled cryogen passing into supply line 11 as it continues out through an exit port 35 where various configurations of cryoprobes are attached.

Although the system may fill or discharge each cylinder 40 individually, any simultaneous fill or discharge, or rate of fill or discharge, may be incorporated into the system. The closed system keeps a supply of liquid nitrogen available for delivery to the cryoprobe and provides a more immediate and rapid rate of cooling for cryotherapeutic procedures. It is therefore possible to close the supply port 29 where supply tanks fill the dewar (See FIG. 1 and FIG. 4) and move the system to any locale or setting. Furthermore, as depicted in FIG. 1, the supply valve 2 may be closed and the release valve 14 opened to create a flow of liquid cryogen to the cryoprobe. Various arrangements of valves and sensors may therefore provide for similar flow.

In one embodiment, the pressurized chambers 40 are filled and the dewar sealed. A single drive pump 1 perpetuates directional flow of the cryogen into the pressurization chambers. In one embodiment, all chambers can be filled through various configurations of single direction pumping. In another embodiment, a reversible pump and fill method allows one pressurized chamber 40 to fill and then the pump 1 flips or reverses functionality to fill another pressurized chamber. This process can be repeated to fill any number of chambers. In addition, the supply manifold can be pressurized to drive liquid nitrogen into the pressurization chamber.

In one embodiment, pressurized chambers 40 are enclosed completely within the dewar 6. However, any arrangement of the pressurized cylinders is possible so long as the closed system provides for the pulsatile delivery of cryogen to the cryoprobe. As such, any single or multiple configurations of cryoprobes or catheters may be used. Such instruments may also include cryoguns or cryodevices for rapid cryo-delivery processes or cryotherapies.

Figure 5:
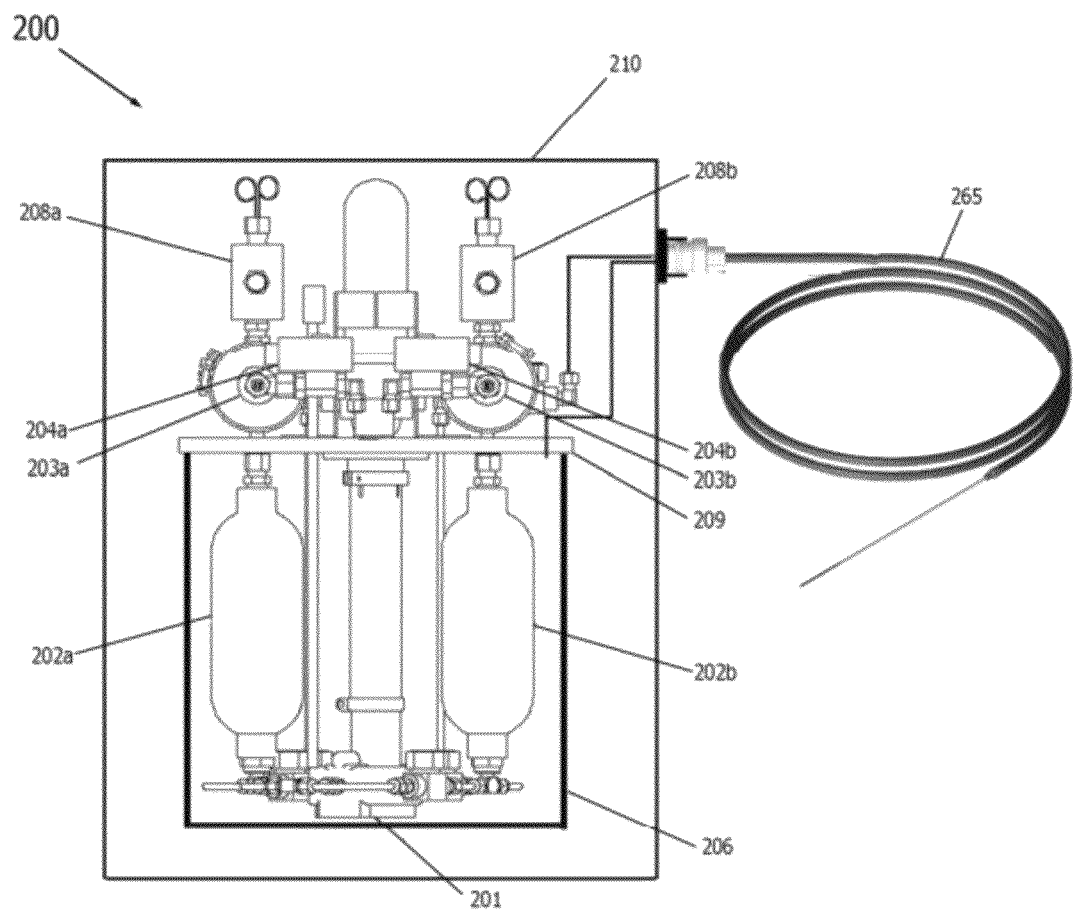
FIG. 5 is a depiction of a front view of the system.

As illustrated in FIG. 5, a cryogenic system 200 (also known as cryoengine 200) has a two cylinder configuration, the system of which is divided into two subassemblies: (I) those components above the cover 209 and (II) those components below the cover. All of the components below the cover are contained in a liquid nitrogen dewar 206 and immersed in liquid nitrogen at atmospheric pressure (BP=−196° C.) during operation. The machinery and components of the operational system are housed in a console 210 to which the cryo-catheters/cryoprobes 265 are attached to form the complete system 200. To understand the operational features of the cryoengine and method of production and transport of supercritical nitrogen (SCN), a brief description of cryogen flow follows.

Upon filling the dewar 206 with liquid nitrogen from an external source, an immersible liquid cryogen pump 201 is activated to fill each cryogen supply cylinder 202a & 202b, or cartridge, sequentially. Initially, one cartridge 202a is filled along with its linked cryogen pressurization cartridge 203a. Cryogenic solenoid valves 204 (a and b) provide venting of the gas within the cartridge assembly to support filling. Manifolds 208 (typically metal, stainless steel or aluminum) provide access points into the cartridges/cylinders 202, 203. The manifolds comprise components such as a heater, thermocouple, and the vent lines that pass through to the cylinders 202, 203. Upon completion of the filling process, the cryogen pressurization cartridge 203a is heated to generate a pressure of about 1000 psi (68 bar). Liquid nitrogen becomes critical at about 493 psi (34 bar) (BP=−147° C.). Pressurization beyond the critical point results in the formation of SCN, a dense fluid with minimal surface tension and capable of near frictionless flow, and with properties that may be tuned to either a gas or liquid.

By converting liquid nitrogen to SCN in a cartridge cooled by atmospheric liquid nitrogen (−196° C.), the SCN is subcooled and tuned to the liquid phase, attaining an excess temperature (i.e. the ability to absorb heat without boiling) of approximately 50° C. When the SCN is injected into the flexible cryoprobe, the SCN flows with minimal friction to the tip of the probe (boiling chamber). In the tip, SCN pressure drops due to an increased volume and outflow restriction, heat is absorbed (nucleate boiling) along the inner surface of the TIP, micro bubbles of nitrogen gas condense back into a liquid, and the warmed SCN reverts to pressurized liquid nitrogen as it exits the return tube and resupplies the dewar containing atmospheric liquid nitrogen. This flow dynamic occurs within a few seconds and is regulated by a high pressure solenoid valve 204. Upon emptying of the first cartridge subassembly (202a & 203a), the process is repeated with the second cartridge subassembly (202b & 203b).

As demonstrated by FIG. 5, the limitations of liquid nitrogen have been overcome by developing a novel device to convert atmospheric liquid nitrogen to supercritical nitrogen. Where liquid nitrogen was previously delivered through large tubes and did not provide for rapid delivery, the current system herein described allows for rapid delivery of liquid cryogens through very small tubing of the cryo-instrument 265. The SCN can be injected or drawn through two plus meters of hypodermic tubing without boiling, thereby resulting in near instantaneous ice formation at the tip to target site specific ablation of tissue as well as the creation of transmural lesions without the formation of a thrombus or aneurysm. Supercritical nitrogen is a dense fluid with properties of both gas and liquid that can be tuned toward one phase or the other. In the liquid phase, SCN lacks surface tension and transports without friction. The above-described technology generates SCN in a pressurized cartridge immersed in atmospheric liquid nitrogen. This cryoengine, which operates as a cryogen generator, produces SCN in the liquid phase with a boiling point of about −149° C. which is subcooled by the surrounding atmospheric liquid nitrogen to about −196° C. When the SCN is expelled from the device to the probe tip, the SCN passes instantly through the system without the phase transition to a gas due to both the frictionless flow and the subcooling which compensates for parasitic heat gain along the path. As such, the embodiment of FIG. 5 may be utilized in any supercooling system or in directing flow of liquid cryogen through to a cryo-instrument. The supercritical point will be determined by the chemistry of the specified liquid or gas used. Therefore, the system can be adjusted to accommodate for differences in chemistry. A catheter/probe assembly 265 is connected to the cryoengine of FIG. 5.

In one embodiment, the design of the cryoablation console is a cryosurgical device that utilizes SCN as the cryogen. The console comprises a vacuum insulated, stainless steel supply dewar (filled from an external source) that stores the reserve liquid nitrogen (LN2). The lid for this dewar is a machined piece of 1" thick delrin backed with a 2" thick piece of foam insulation. A 3" flexible duct vents the nitrogen gas from the dewar directly out the bottom of the console. A small, brass gear pump driven by a 24V DC motor pumps the LN2 through a series of check valves, preventing pressure from escaping back through the pump, and into a stainless steel supply cylinder. The nitrogen gas generated during filling is vented through two low pressure solenoid valves (the LP vent valves) before entering a heat exchanger with the exit located inside the console. The LN2 level in the supply cylinder is monitored by a multi-point thermocouple probe which reads the temperature at the bottom, middle, and top of the cylinder as well as at a point just above the lid inside the main vent line. A second stainless steel cylinder (the pressure cylinder) is located outside the supply dewar and is connected to the supply cylinder through a high pressure solenoid valve (the pressure valve). This valve is closed during filling to prevent cold nitrogen gas from entering the pressure cylinder, but opened during pressurization to increase the total volume/pressure head of pressurized SCN. The cylinders may take the form of any container, any shape and size; here, utilized cylinders have been 1 L, 2.25 L, and 5 L, although any size and dimension will work. In practice, however, the footprint of the operating device in a clinical operating environment is as small as possible. Volume may be based on specific applications, number of procedures and size limitations of the operating environment.

In one aspect, during the pressurization phase, the vent valves are closed, the pressure valve is open, and two cartridge heaters submerged in the supply cylinder are turned on. Heating tape is wrapped around the pressure cylinder, and together the heaters supply enough energy to the closed system to create supercritical nitrogen (SCN). Once adequate pressures are obtained (~1000 psi), two high pressure normally closed solenoid valves (injection valves) can be opened which supply nitrogen to the 2 probe ports. Pressures are monitored by a pressure transducer located in a manifold at the junction of the vent and pressure lines. A pressure bleed valve set to ~1200 psi is also located in this manifold and prevents overpressurization of the system.

In another aspect, the cryoengine also contains a thaw feature. At the bottom end of the pressure cylinder is an in-line gas heat exchanger wrapped with copper tubing. In another aspect, thawing can be achieved by the placement of a thermoresistor wire, film, or coating on the inside or outside of the cryorobe which when activated results in a probe surface heating and thawing of the surrounding area. After completion of the freeze cycle, residual nitrogen gas is passed through this heater and high pressure solenoid valves control flow into the injection line of the probe ports. Upon completion of the freeze/thaw cycle there is ~500 psi of residual pressure in the system. A high pressure normally closed solenoid valve (the HP vent valve) connected through the manifold is then opened to vent this pressure down to a point at which the LP vent valves can be opened to return the system to atmospheric pressure. The console also contains an oil-less vacuum pump connected to the vacuum line of the probe ports that supplies insulation and a safety feature for the probes, and a purge line for flushing warm nitrogen gas throughout the system prior to operation. The pump may also be connected to an operating room vacuum system if desired.

Figure 17:
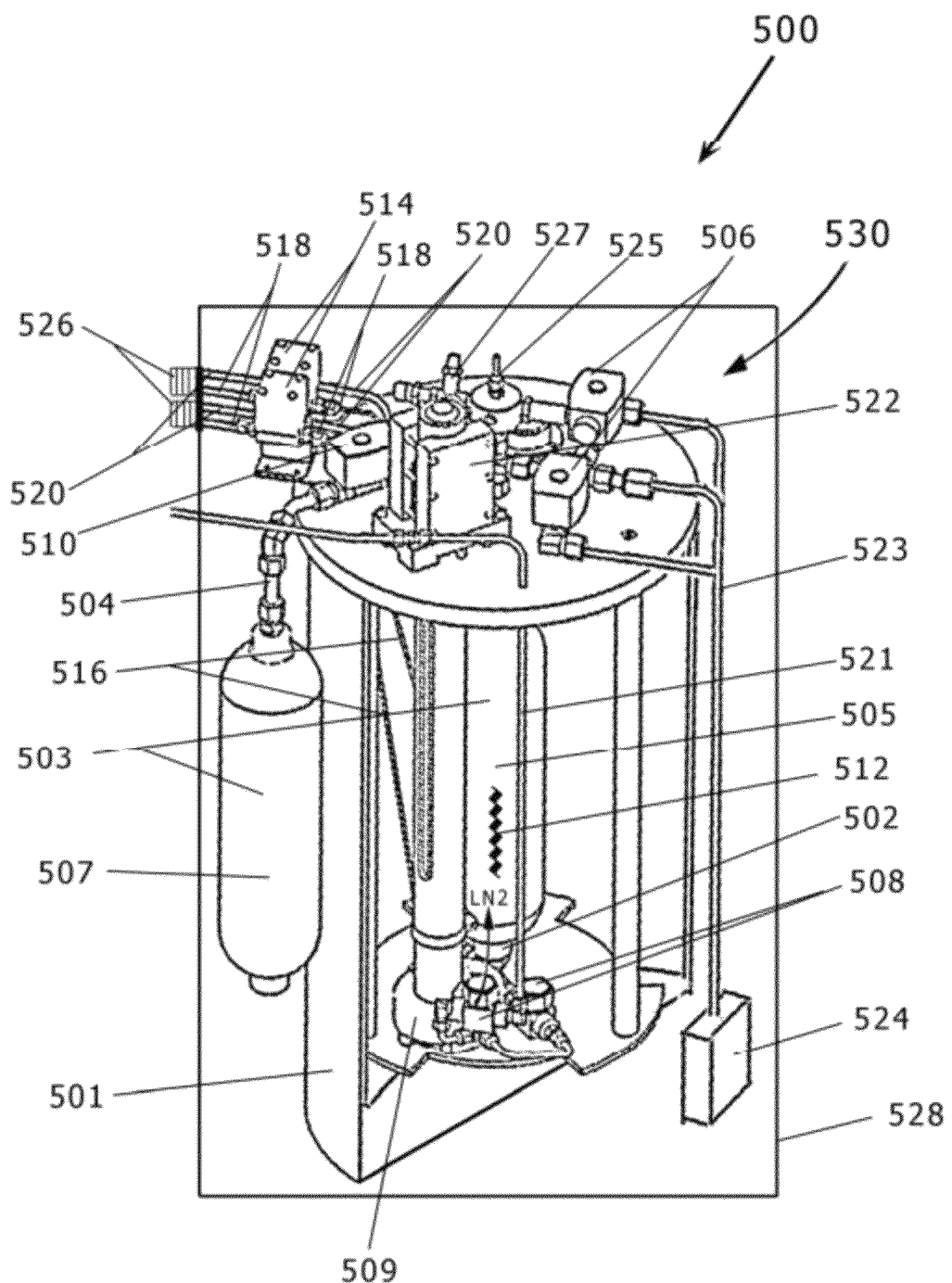
FIG. 17 is an embodiment of the cryogenic system.

A contained cryogenic medical system 500 of the invention is illustrated in FIG. 17. Within the console 528 is a cryoengine 530 (similar to the cryoengine 200 of FIG. 5). A dewar 501 is filled with liquid nitrogen (LN2) to create a cryogen reservoir 501. A pressurization system 503 utilizes a first vessel 505 and a second vessel 507 interconnected by line 504 and having a valve control 510 (which connects the two vessels 505 and 507). In this embodiment, the first vessel 505 is positioned vertically inside the cryogen reservoir/dewar 501. The second vessel 507 is positioned vertically outside the cryogen reservoir 501 at an ambient temperature with the surrounding air. A cryogenic flow actuator 509 is positioned inside the cryogen reservoir. The cryogenic flow actuator 509 is activated by engaging the fill motor 522 to start the flow of the LN2 through a fill valve 508 (here, a check valve for uni-directional flow), thus creating a flow of LN2 from the reservoir 501 into a port 502 of a first vessel 505 of the pressurization system 503. Valve 508 may include sensors for temperature and pressure monitoring and/or control. When filling the first vessel 505, a vent valve 506 connected to the first vessel 505 is opened to allow venting of any excess vapor created during the fill process, the gas of which escapes through vent lines 523 to the vent fan 524.

The level of liquid nitrogen within the first vessel 505 is measured by a thermocouple sensor 525 which protrudes through the first vessel 505. Several means are capable of being utilized to sense the liquid and gas cryogen levels within the vessels 505/507. Such sensors may include a float sensor, a capacitance level sensor, thermal sensor or similar variations thereof. Following filling of the first vessel 505, the vent valve 506 is closed and the valve control 510, positioned between the first vessel 505 and the second vessel 507, is opened to create a continuous pressurization system comprising a volume of liquid nitrogen in the first vessel 505 and an approximately equal volume of nitrogen vapor in the second vessel 507.

In this embodiment, the first vessel 505 is at near LN2 temperatures; whereas the second vessel 507 is at an ambient temperature above the temperature of the first vessel 505. In another aspect, the temperature of the second vessel 507 is elevated to an above ambient temperature. In yet another aspect, and without limitation, the temperature of the second vessel 507 is kept at temperatures in the range of about 30° to about 40° C. to help build the pressure faster as compared to when lower temperatures are used.

Figure 18:
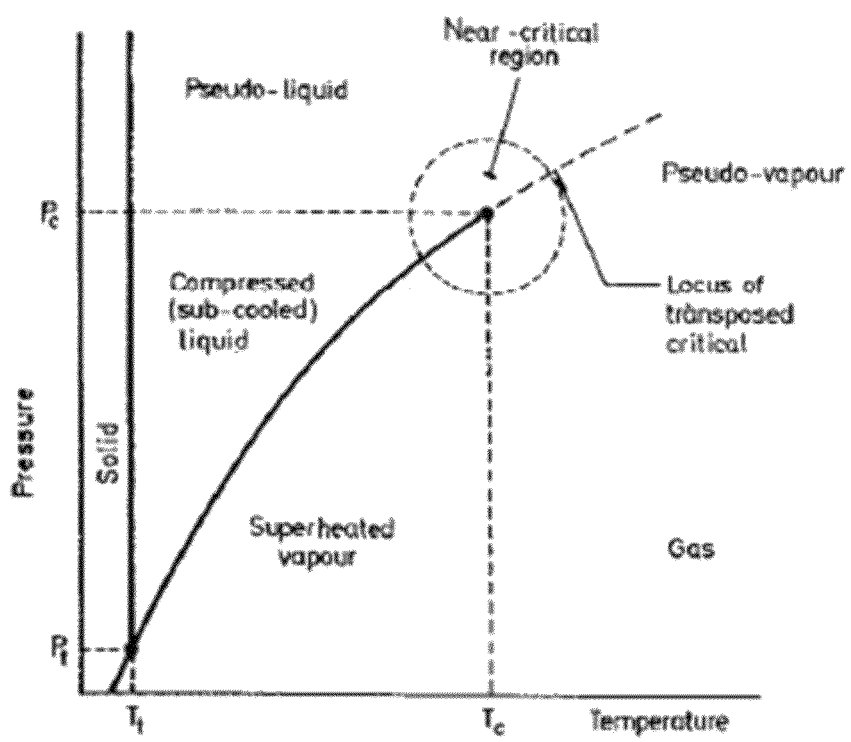
FIG. 18 is a chart describing various thermodynamic regions.

A heater 512 is arranged internal to the first vessel 505 and activated to create a boiling microenvironment in the LN2 to produce N2 gas. Since the first vessel 505 and the second vessel 507 form a closed pressurization system 503, the boiling of the LN2 results in gas expansion and thereby increases the pressure within the pressurization system 503. The pressure in the system is increased through and beyond the critical point of nitrogen (−146.95° C. at 492.9 psi), creating supercritical nitrogen (SCN), also known as a psuedo-fluidic state (pseudo-gas or pseudo-liquid) in the art. See FIG. 18 (PRIOR ART) which describes the various thermodynamic regions; Reference: Hands, B. A. *Cryogenic Engineering, Academic Press,* 1996.

Novelty in the cryogenic system 500 is in part due to starting with near equal volumes of LN2 and N2 vapor as components for the creation and maintenance of supercritical nitrogen (SCN). Once SCN is produced and a pressure of about 1,000 psi or greater is achieved within the pressurization system, control valves 514 are opened to allow the flow of SCN from the pressurization system 503 through to cryolines 516/518, thus creating a fluid path of SCN toward the connection sites 526 for externally positioned probes. In the illustration of FIG. 17, the connection sites 526 are positioned for easy access on a console 528 which encases the entire pressurization system 503, including the components described herein.

A pressure bleeder valve 527 prevents excess pressure build-up before the valve 514 is opened. Typically, the pressure bleeder valve 527 is set at about 1250 psi or anywhere around that pressure, up to the burst pressure of the material utilized in the pressurization system.

As illustrated in FIG. 17, the cryolines 516 are immersed in the surrounding LN2 reservoir 501 and create a continuous fluid path from the first vessel 505 of the pressurization system 503 to the external cryoprobe(s). The flow of the SCN through the cryolines 516 is controlled by the control valves 514.

The cryogenic system and process described allows for delivery of SCN through cryolines 516, specifically through supply tubing 518, which extends over distances of about two to three meters or greater in length to a designated freeze region in an external cryoinstrument, or cryoprobe (not illustrated in FIG. 17). In addition, the system 500 provides for the delivery of SCN through ultra fine capillary-like tubing (not illustrated) that connects to the connection sites 526 for supplying SCN to externally positioned probes. The flow occurs in a matter of seconds providing for the delivery of ultracold SCN to the probe tip. The SCN is then returned through a second fluid path 520, or return tube 520 and recycled/returned/reclaimed in the LN2 reservoir within the system. The cryogen returns to the reservoir 501 at an ultra cold temperature at a reduced pressure, facilitating the conversion back into LN2 for reuse.

Differential starting volumes of vapor and liquid, when placed under increased pressure above the critical point, results in the creation of mixed or different physical states. This results in a condition which is difficult to maintain and control. For example, a starting volume ration of 1:1 LN2:N2 vapor when pressurized to 1,000 psi results in the generation of SCN. Whereas a starting volume of 3:1 LN2:N2 vapor when pressurized to 1,000 psi does not create SCN because although it is above the critical pressure it does not exceed the critical temperature. When pressures at or near the critical point of nitrogen (492.9 psi) are utilized, the starting liquid to volume ratio increases in importance. Operating in this region of pressures and temperature create an undefined and uncontrollable variable state which has been referred to in the art as "near critical nitrogen". By controlling the volumes, pressures, and temperatures as described herein the present invention overcomes certain deficiencies of the prior art by creating a stable and controllable source of SCN, compressed LN2, or pseudo-liquid.

Generation, utilization and controlled delivery of SCN allows for the rapid delivery of a cryo-treatment, offering the speed of cold temperature gas and near critical cryogen/nitrogen while providing the heat extraction, work capacity, of a LN2 system.

The cryogenic flow actuator 509 is designed to actuate flow of LN2 from the reservoir 501 into the pressurization system 503 to fill the pressurization system 503 (including vessels 505 and 503). The term, pump, is used to describe the creation of movement of the LN2 (see FIG. 17) from the reservoir 501 into the pressurization system 503 through port 502. There is no compression or pressurization of the LN2 within the pump/generator 509; in other words, the pump does not create SCN nor does the pump have the force to drive the LN2 down the supply tube fluid path to the probe tip. The pump is a means to fill a first vessel 505 with LN2.

In one aspect, prior to operation of the cryogenic system 500, purge line 521 is used to blow nitrogen gas through the system prior to filling the dewar 501. The vent fan 524 described increases the temperature of the nitrogen gas that is released through the vent valves 506. Vent lines 523 connect the vent valves 506 to the vent fan to control the temperature. An ambient [warmer] temperature can then be maintained within the console 528.

Figure 6:
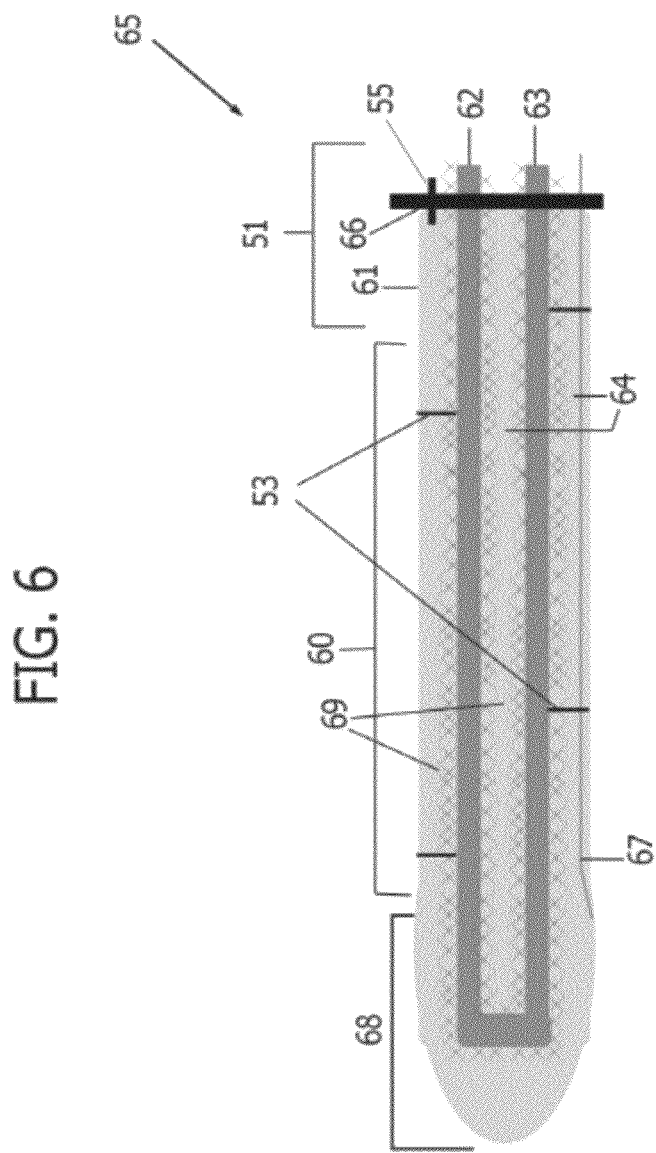
FIG. 6 is a side view of an illustrative embodiment of the device of the disclosed invention when the lumen is filled with particles in gaseous state.
Figure 7:
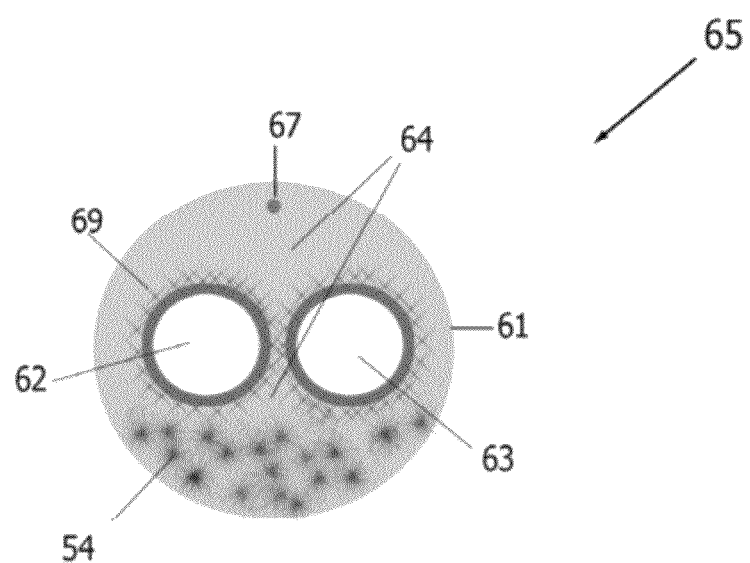
FIG. 7 is a cross-sectional view of the illustrative embodiment in FIG. 6.

The system further comprises attachable or integral cryoprobes or cryocatheters, termed cryoinstruments for various embodiments that may be utilized. An external view of a cryoinstrument 65 of the cryogenic system in accordance with one embodiment of the invention is shown in FIG. 6 and FIG. 7. The cryoinstrument 65 takes the form of a catheter having a tube within a tube configuration, and forming the longitudinal body 65. The longitudinal body 65 comprises internal tubes, including a supply line 62 and a return line 63, contained within an outer insulation tube 61 and continuously running through the length of the tubular shaft 60 of the longitudinal body 65. The outer insulation tube 61, or outer catheter sheath 61, defines the size, shape, and dimensions of the longitudinal body 65 which conforms to dimensions that are capable of housing the internal lines 62, 63. The tubular shaft therefore extends from a proximal end 51 of the longitudinal body 65 to a distal end or tip 68. The outer catheter sheath 61 provides a unitary support structure for the flow of cryogen to and from the distal end of the catheter tip 68; desirably, the distal end is where a freezing event is initiated. The cryogen utilized in one embodiment may be liquid nitrogen. In another embodiment, supercritical nitrogen is utilized. Any desired liquid cryogen may be utilized, however, and the system adjusted to accommodate for different chemistries and phases of matter.

The inner supply line 62 and return line 63 are maintained in the center of the outer sheath 61 by open configuration insulative spacers 53 placed throughout the catheter 65. The spacers 53 can be in the form of individual units, tube extrusions, or other means of positioning the tubing. The open configuration allows for a catheter lumen 64 to be filled with gas. The outer catheter sheath 61 is sealed to the connector 66 to create the gaseous lumen 64. The tip 68, in combination with the inner supply line 62 and the return line 63 come into contact with the outer sheath 61 at the distal end to develop a freezing region. Additionally, the open configuration can also allow for a vacuum to be drawn upon the catheter lumen 64.

In addition, in one embodiment, the shaft 60 of the catheter 65 is flexible, as facilitated by a deflection wire 67 that runs along the shaft 60, the shaft of which is insulated by a temperature induced vacuum. The deflection wire 67 is a control line that runs down the shaft 60 to the tip of the catheter 65 to allow the catheter tip 68 to be moved on an angle, in a finger-like motion to steer and direct the catheter/probe 65 to the target tissue. In one embodiment, the deflection wire 67 guides the device 65 and monitors environmental measures of temperature, pressure, and/or physiological conditions. The guide 67 may integrate individual components and sensors such as an optical imaging component in connection with the guide or any number of thermocouples, pressure transducers, electrocardiogram monitors, or other electrophysiological sensors, alone or in combination.

Another embodiment of the present invention may use insulative foam (e.g. styrofoam, plastics, rubberized materials or other such insulative compositions) to separate the outer shaft 60 from the internal lines 62, 63 (i.e. inner supply line 62 and return line 63). Various aspects of the invention, however, accommodate a catheter tip 68 as designed to be steerable and deflectable to allow for guided targeting to the desired tissue site. In one aspect, spacers or insulative foam may be utilized to prevent internal supply and return lines from contacting the outer sheath. In another aspect, any freeze zone can be produced as designated by the configurations of catheter tips 68. (See FIGS. 10-13).

In the process of utilizing the catheter 65 of the present invention, a condensation based vacuum insulation is temperature dependent and located in the catheter 65. Upon the outer surfaces 69 of the walls of the supply line 62 and return line 63, a process of physically marking or chemically etching the surfaces 69 enhances nucleation and physical vaporization deposition of saturated gas. For exemplary purposes only and not limitation, the surface may be roughened, sprayed with any number of powder-like substances like silica, metallic particles and/or a carbon coating. The lumen 64 within the outer sheath 61 is filled with select vapors, or non-equilibrated phase change gas 64. In this embodiment, for example, butane is utilized which remains in a gaseous state at about room temperature, between about 0° C. to about 37° C. (See FIGS. 6, 7), but solidifies into crystalline deposits 52 upon chilling to below about 0° C., specifically to about −138° C. for butane, and simultaneously deposits a film of crystals in a controlled deposition process upon the designated surfaces 69 (See FIGS. 8, 9). Butane solidifies at about −138° C., a critical point for butane. It should be noted, however, that the temperature variations are dependent upon the type of vapors utilized, chemical characteristics and variations of vapor combinations. Therefore, temperatures of varying gases may be selectively controlled so as to create the same or similar effect of spontaneous nucleation and simultaneous deposition upon reaching a freezing temperature. One novelty of the system allows the hypotubing to get cold enough for this vacuum to form such that the hypotubing remains structure and function for procedural use.

In addition, one embodiment may interconnect a vacuum line of a cryo-system console with the catheter or probe 65 through a vacuum port 55 of the connector 66 as illustrated in FIGS. 6 and 7. In one aspect, the vacuum is formed upon sealing the lumen at the connector and mechanically drawing a vacuum through vacuum port 55. In another aspect, the vacuum port may connect via its own vacuum system or in combination with the vacuum pump of the cryosystem, or through a hospital vacuum system. Thus, a dual insulative barrier can be created in the present invention by either a mechanically drawn vacuum or a spontaneously induced vacuum [via temperature inducement] (the vacuum itself creating the insulation for the internal tubes) in combination with a nucleation enhanced surface modification to enhance deposition of gas crystals onto the designated outer surfaces of the internal tubes. Desirably, the outer walls of the internal tubes are physically or chemically etched at designated sites along the tubular shaft. A region within the distal end or tip 8 can then be configured specifically designated freeze zones.

In one embodiment, heating wire or heating tape is used on the external sheath of the catheter to keep its temperature about freezing, 0° C.

Figure 8:
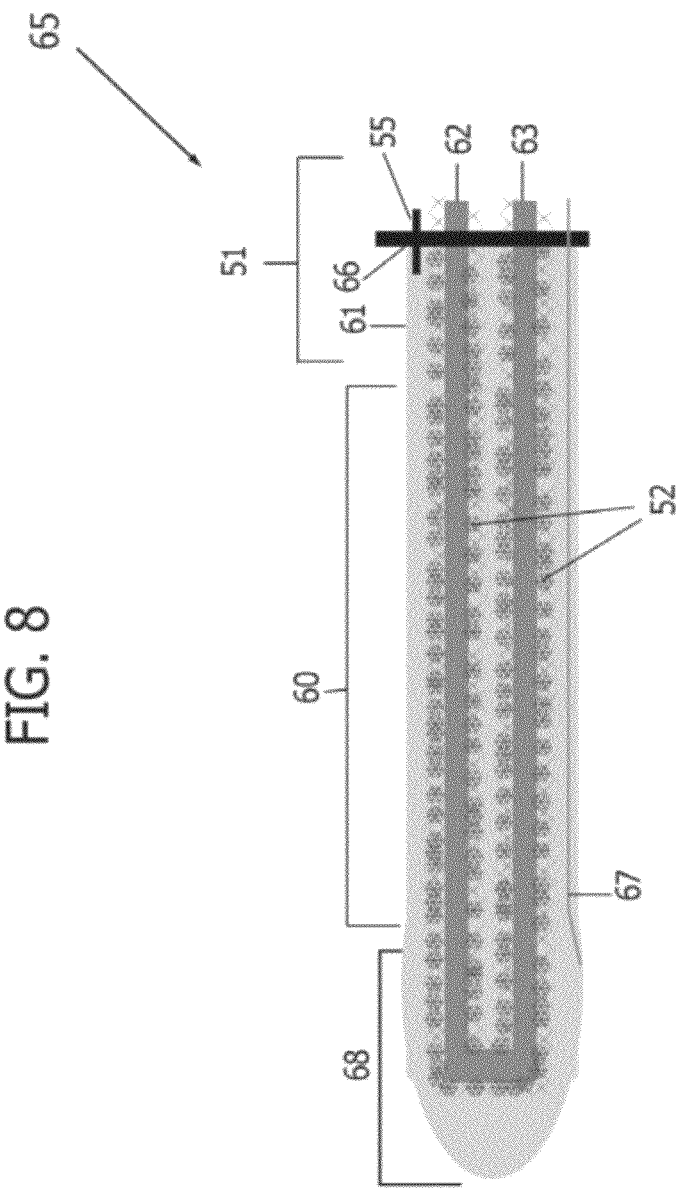
FIG. 8 is a side view of an illustrative embodiment of the device of the disclosed invention as temperatures are reduced to a freezing point of the particular gas selected.
Figure 9:
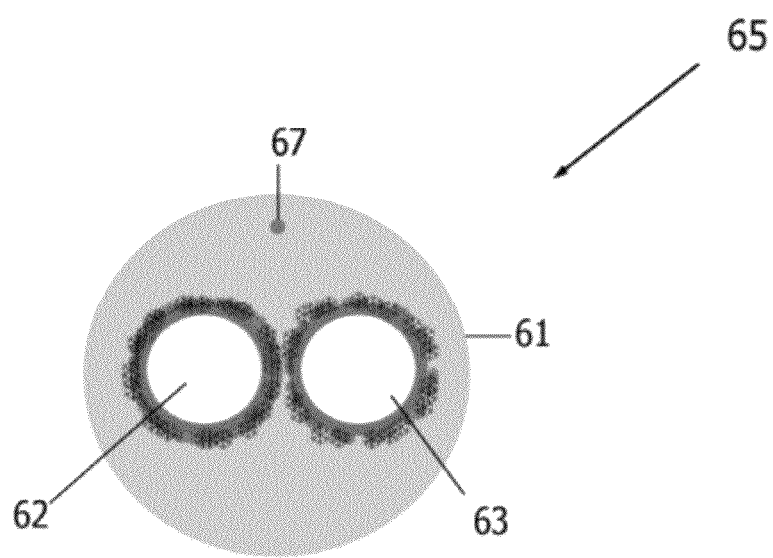
FIG. 9 is a cross-sectional view of the illustrative embodiment in FIG. 8.
Figure 10:
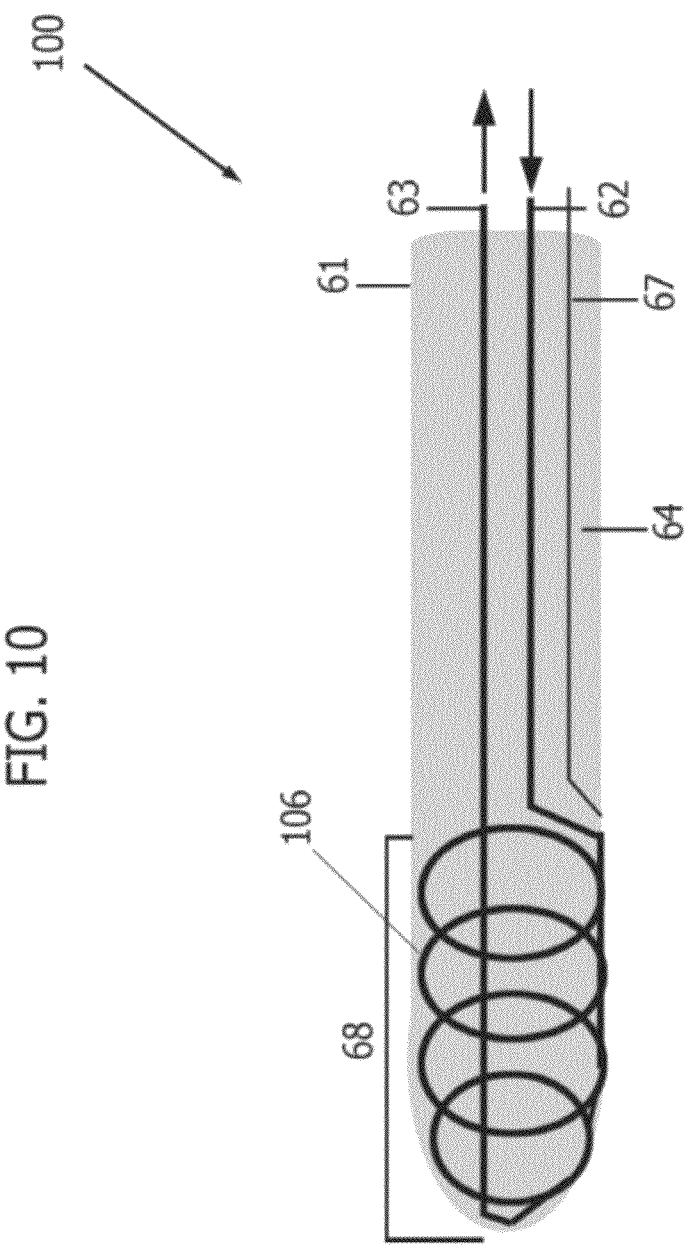
FIGS. 10-13 are side views of various embodiments of a device of the invention.

In the described embodiments, nucleation/sublimation in combination with a deposition process forms solid crystals along the supply line 62 and return line 63 outer walls, and spontaneously results in an evacuated space within the lumen 64. The evacuated space acts as an insulative barrier between the outer catheter sheath and the frost encased inner lines 62, 63. Film wise deposition along a length of the surfaces 69 of the supply line 62 and return line 63 results in crystalline film deposits of low thermal conductivity. The deposition may coat a portion of the outer surfaces or the entire outer surfaces of the inner lines to run the entire length of the internal tubes. (Note: The 'x' marks in FIGS. 6, 7 demonstrate the nucleation enriched supply and return tubular surfaces 69, the tubular surfaces of which are modified by processes described herein. The non-solidified gas crystals 54, non-equilibrating phase change gas particles 54, are illustrated in FIG. 7. Nucleated or solidified particles, as designated by "*" are depicted in FIGS. 8, 9 upon the modifications "x" (etching) on the surfaces 69. The nucleated particles 52 (marked as "*") are formed when the gas reaches a freezing temperature. In one aspect, any pressure may be utilized. For exemplary purposes and not limitation, pressure in the device may be maintained or controllably elevated or reduced. For instance, gas may be maintained at atmospheric or high pressure to support the retention of the vapor state at room temperature.

Other aspects of embodiments of the present invention include gas as either a pure component or as a mixture of various components. Such gaseous compositions, for exemplary purposes only and not limitation, may comprise butane, carbon dioxide, iodine, camphor, and/or nitrous oxide.

In another embodiment, an enhanced nucleation surface 69 on inner tube/line 62, 63 surfaces may result where a process includes treating the walls of the inner lines 62, 63 to match nucleating efficiency with the chemical characteristics of the gas to be deposited (e.g. marking the surfaces with impurities, utilizing silica, or other powderized material, chemically coating or etching) and thereby create a similar effect.

Embodiments of the present invention manipulate the structural configurations of the tips 68, as illustrated in FIGS. 10-13. In one or more embodiments depicted, the freeze zone is created where the internal components 62/63 contact the outer sheath 61 at a distal end 68. One such embodiment of a distal end 100 in FIG. 10 includes a closed loop coiled supply tube 106 in contact with the outer sheath 61 to affect a cold sink. The supply line 62 and return line 63 convene at the freezing zone of the tip in the formation of a coil 106.

Figure 11:
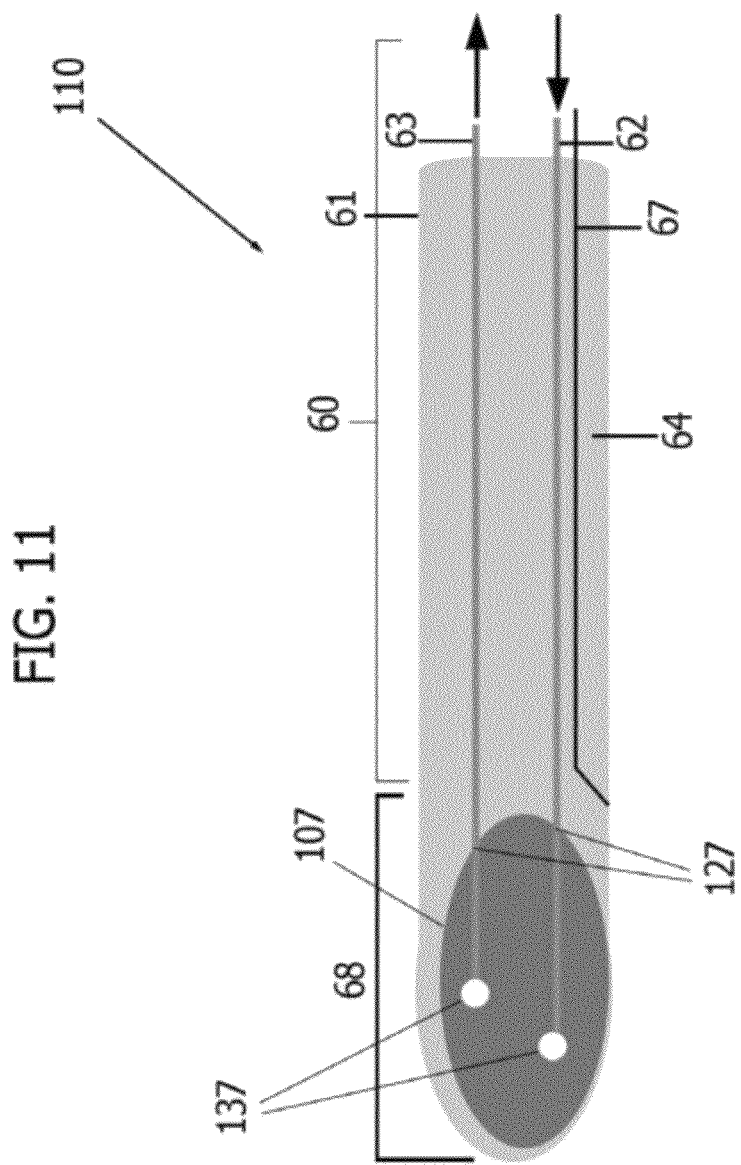

In another embodiment of a distal end 110, as shown in FIG. 11, a metallic balloon tip 107 is illustrated in which cryogen is circulated in the tip and then returned. The supply line 62 extends to a distance into the tip 68 beyond the extension of return line 63 such that cryogen pumped into the balloon-like tip 107 circulates within the sealed confines of the inflated region when the catheter is engaged for the procedure. The supply line 62, however, can extend any length or distance into the tip. The balloon-like tip may be composed of any flexible or rigid material including metallic, plastic, or ceramic compositions. Similarly, the balloon-like structure within the sheath may cause the outer sheath 61 to inflate and deflate for cryogenic procedures. For example, and not limitation, cryogenic procedures performed within a vessel may advantageously make use of an inflatable cryogenic element 107 at the distal end of the probe so that the outer sheath expands as the internal inflatable cryogenic element expands.

Also depicted in FIG. 11, the inflatable tip 107 is a sealed within the distal portion 68 in connection with both an individual supply line 62 and an individual return line 63. The embodiment of the distal end 110 is included in the length of the longitudinal tube and has a distal tip 68 which serves as the freezing region in connection with the tubular shaft 60 (only a portion of which is illustrated here in FIG. 11) (i.e. In the embodiment shown in FIG. 14, a distal end 128 can be replaced with distal end 110.) A sealed interface 127 ensures that the inflatable area can expand and contract in correspondence with the fill and removal of the cryogenic medium. The cryogenic medium in one embodiment in liquid nitrogen. Any cryogen may be utilized, however, to accommodate the demands of the system and treatment measures. Further, the inflatable structure, here, a metallic balloon tip, is designed and configured with materials that conform to the use of liquid nitrogen. Without considering the type of cryogen utilized, the inflatable tip may rupture or create undesired effects. For exemplary purposes, and not limitation, the tip of the present embodiment is designed to meet the needs of a system and device utilizing liquid nitrogen.

Another aspect of the probe/system in FIG. 11 is that the sealed interface 127 may be a wall or connection component (not illustrated) which seals the freezing region 68 of the tip away from the tubular shaft 60 in a blunt-tip probe. The sealed interface allows a supply line 62 and a return line 63 to access the freezing tip, the open ends 137 of which allow cryogen to be dispersed within the sealed zone 68. In FIG. 11, the sealed zone is the balloon tip, but any size or shape of sealed zone may be utilized in different aspects of the present invention to create similar results. It should be noted that the open-ended supply line in one embodiment extends further into the sealed zone toward the distal end and beyond the open end of the return line. Any length of supply line or return line, however, may be utilized; the lengths may be designed having equal lengths or different lengths, as desired.

Figure 12:
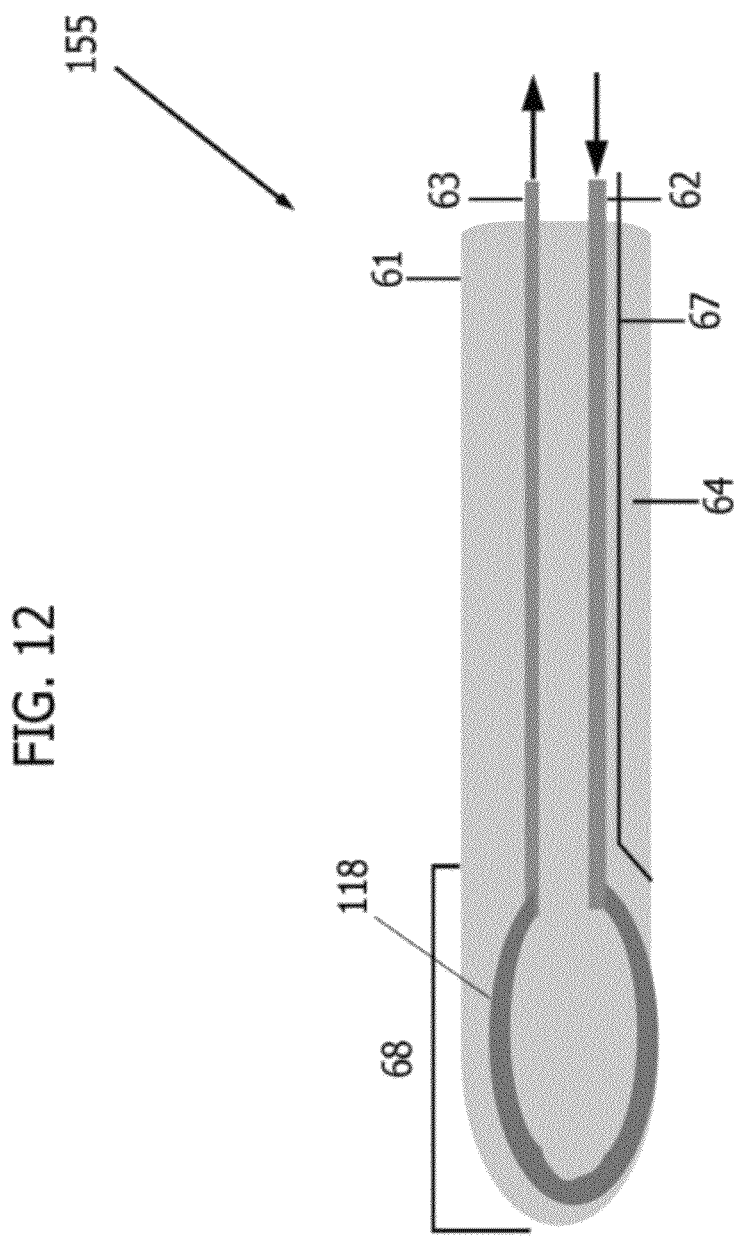

FIG. 12 is another embodiment of the probe tip/distal end 155 which illustrates a closed loop tip 118. The closed loop tip integrally connects both supply line 62 and return line 63 to form a unitary structure for delivery and return of liquid cryogen to the distal end in the freezing region of the probe. In the tip, SCN pressure drops due to an increased volume and outflow restriction, heat is absorbed (nucleate boiling) along the inner surface of the tip, micro bubbles of nitrogen gas condense back into a liquid, and the warmed SCN reverts to pressurized liquid nitrogen as it exits the return tube and resupplies the dewar containing atmospheric liquid nitrogen. Temperatures and pressures within the return line are maintained by the system to allow for recovery of LN2 at near ambient pressure within the dewar following utilization. The cryogen within the dewar is at nominally ambient pressure and at a temperature at about −196° C., or in the range of about −160° C.+/−40° C.

Figure 13:
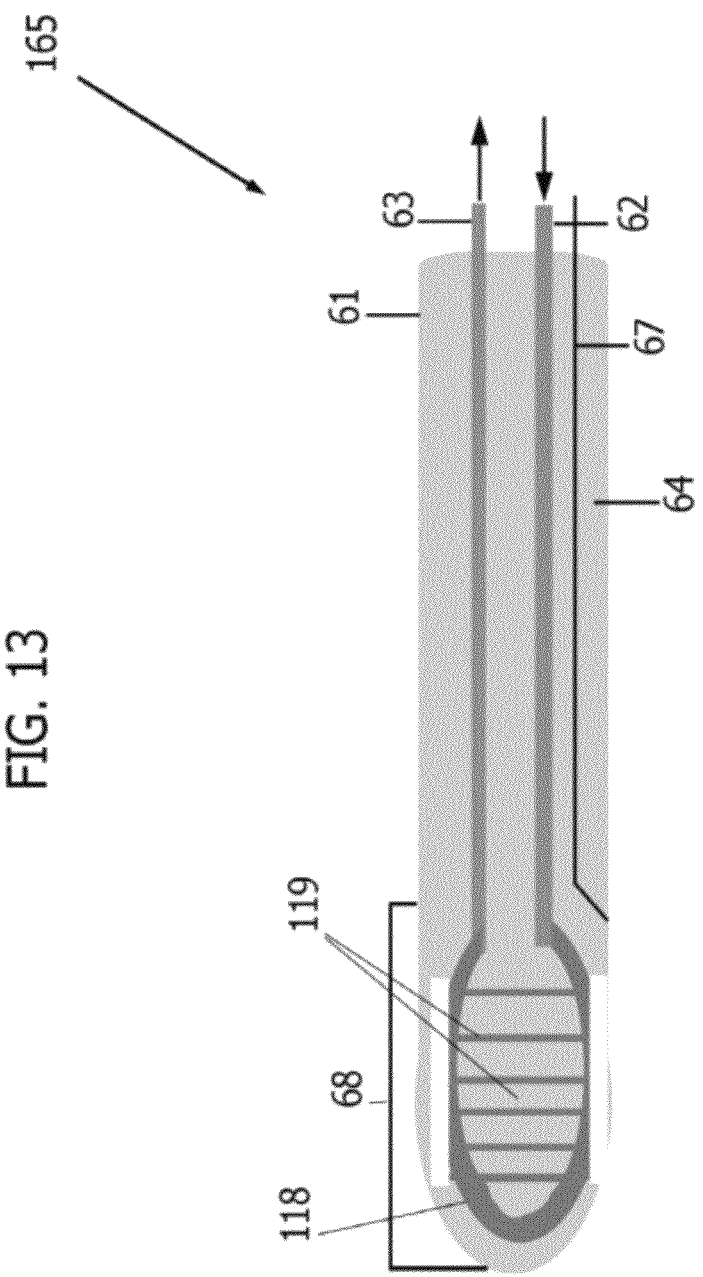

FIG. 13 illustrates a cryoprobe 165 as a closed loop tip with a finned heat exchanger 119 within the freezing zone or tip 68. The heat exchanger provides for a more efficient heat extraction from the tissue, thereby providing faster cryotreatment and greater injury/freezing to the tissue site. The heat exchanger is also utilized to cool the cryogen prior to return to the console, resulting in increased cryogen recovery. Other variations in tip design may be any size and dimension or take the size or shape of known catheters or probes 65 in the field. For exemplary purposes and not limitation, in cancer therapeutics, cryoprobes are utilized to ablate the target tissue. In cardiac applications, catheters or surgical probes are utilized in the cryoablation procedure. Further configurations of the cryoprobe as described infra may also accommodate other structural variations.

In another embodiment, the configuration of the tip is an expandable net to encircle the ice ball and capture any ice fragments that break away (not illustrated). The net would maintain a static environment around the probe tip to facilitate ice formation.

Figure 14:
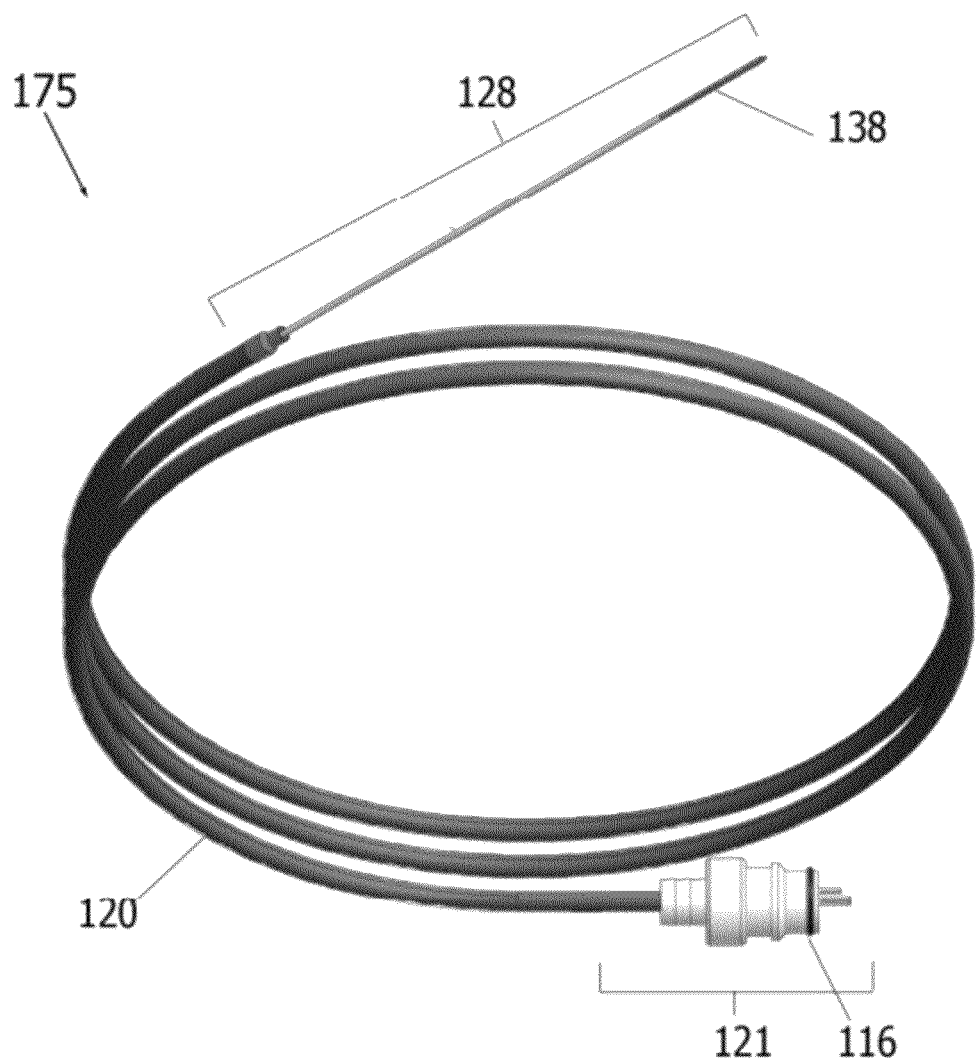
FIG. 14 is an illustrative embodiment of a product of the present invention.

As demonstrated in FIG. 14, the product for performing cryotherapeutic procedures is illustrated as an elongated body 175, about six to eight feet in length. A connector 116 at a proximal end 121 allows the cryoprobe to be connected with a cryogenic delivery system 200 (see FIG. 5). The freezing region, or tip 138 is position within the distal end 128 with a flexible tubular shaft 120 (also known as an umbilical) positioned between the ends. (Some of the various embodiments of distal end 128 have been depicted in FIGS. 10-13, embodiments of distal ends 100, 110, 155, 165 which can serve as replacements for the distal end 128 within the elongated product 175. The body 175 comprises an outer sheath (as illustrated in FIGS. 6 and 7) with one internal tube (supply tube) configured inside the sheath to deliver cryogen to the freeze zone at the target tissue site; a spacing between the centrally positioned internal supply tube and outer wall of the tubular shaft 120 returns liquid cryogen from the freeze zone. For exemplary purposes only, and not limitation, the supply is central to the surrounding coaxial return line. The cryogenic delivery and return lines, however, may be configured in various arrangements (i.e. vice versa arrangement). The lines may also be positioned adjacent one another. When in use and hooked to a cryogenic delivery system, the product 175 simultaneously produces an insulative vacuum throughout the tubular shaft 120. A dual insulative barrier is formed by a temperature initiated transient vacuum in combination with an enhanced nucleation deposition process along the outer surface of the internal tubes (discussed infra). The nucleation sites are therefore capable of selective placement anywhere throughout the product. Additionally, an external active vacuum may be used in conjunction with the transient vacuum or as a stand-alone feature. Cryogenic catheter or probe insulation may also be achieved through an actively drawn or permanently drawn vacuum.

In one embodiment, the distal end 128 is a needle-like probe end. In another embodiment, the distal end 128 takes the form of a blunt-tip probe end. The distal portion 128 may be integral with the tubular shaft or be removably placed in connection therewith. The interconnections of proximal connector, tubular shaft, and distal probe ends thus determines whether or not the individual parts, alone or in combination, may be reused, or disposed of. Further, the length of the distal end 28 may vary according to treatment procedure and may be any size, shape and dimension to correspond to the tissue treated.

Figure 15A:
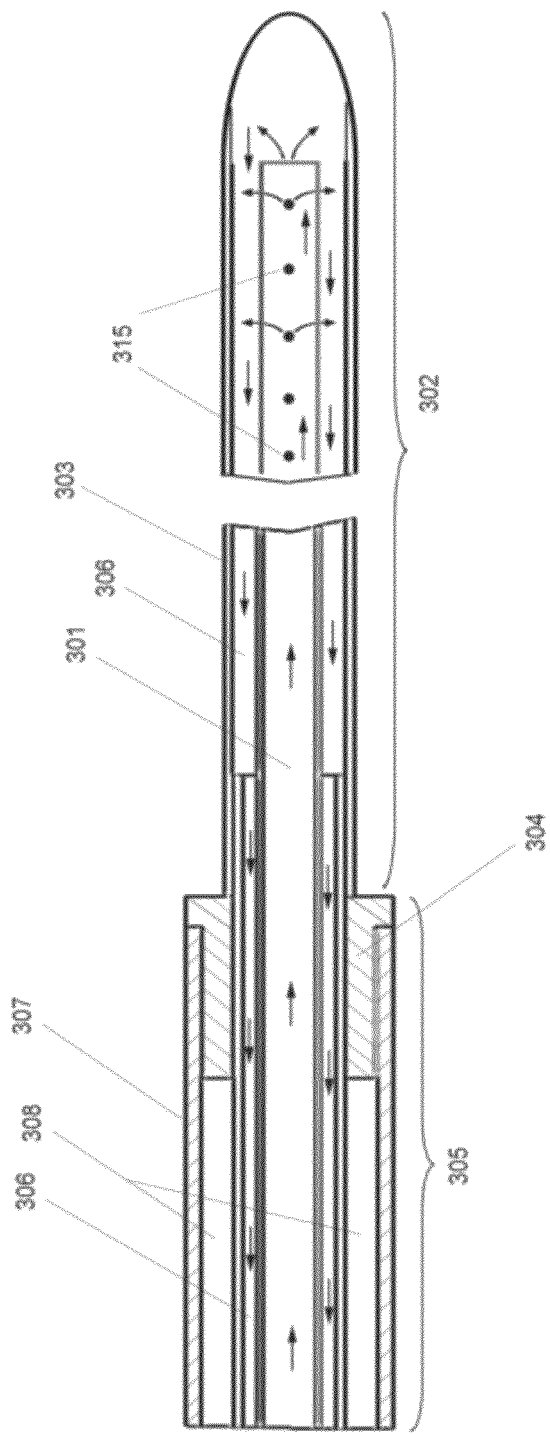
FIG. 15A is a magnified view of an end portion from FIG. 15.

As shown in FIG. 15, one embodiment of the cryoablation device takes the form of a surgical cardiac cryoprobe 300. Operating the cryoablation device as a surgical cardiac cryoprobe 300 utilizes supercritical nitrogen (SCN), high pressure liquid nitrogen with a pressure of about 1000 psi and temperature range of about −210° C. to about −100° C., as provided by the cryoablation console (shown in FIG. 5). The high pressure SCN is passed through to a micro-lumen supply tube 301 into a boiling chamber, or probe tip 302 (See FIG. 15A). The SCN supercools the target tissue by extracting heat from the tissue at a rate consistently greater than any cryodevice currently used in the art. At the tip, the pressure varies from about 0 psi to 1000 psi depending on the operational state. Freezing specifically occurs at probe tip 302 that has a non-insulated outer casing 303 which provides a heat exchanging surface. The joining tube 304 (see magnified view in FIG. 15A) separates the probe tip 302 from the insulated tube portion 305. The joining tube 304 is a plasticized material, but any joining component may be utilized including solder or adhesive. The SCN is evaporated by incoming heat from surrounding tissue and then returned to the console by way of a micro-lumen return tube 306. Both supply tube 301 and return tube 306 are housed in a coaxial fashion within an outer sheath 307. In another aspect, however, the tubing, supply and return tubes, may be positioned side-by-side in a parallel configuration.

As shown in FIG. 15A, the flow path through the supply tube (→ →) demonstrates the movement of SCN toward the distal tip 302. The return arrows nearest the outer casing 303 illustrate the nitrogen returning on an external coaxial path away from the distal tip. The annulus 308 between return tube 306 and the outer sheath 307 is maintained under vacuum to minimize unwanted heat along the fluid paths. The tubing is terminated and interfaced with the console (not depicted here) using a high pressure cryogenic coaxial connector 320. The connector may extend and contract in a telescoping fashion to provide a secure flexible or rigid leak-proof connection.

Initially, tip pressure ranges from about 800 psi to about 1200 psi, and achieve temperatures of less than about −150° C. within 20 seconds. When the cryogen is collected within the dewar following return, the final pressure is near or at ambient pressure and the temperature of the cryogen bath is nominally at about −196° C.

In addition, the surgical cardiac probe 300 is outfitted with a probe handle 310 at a tubing interface 311. The interface 311 may be flexible or rigid; current design utilizes a brass or metal material with hose barbs to prevent the connection from sliding away from the tubing. Any material conducive to cryo-applications, including plastic or rubberized components, however, may be applicable. In one embodiment, the plastic probe handle 310 houses an electromechanical assembly, or trigger 312, for the user's remote control of the cryoablation (e.g. physician triggered ON/OFF control). An electronic display provides information regarding the device and procedure. For instance, the probe temperature is captured by a T-type thermocouple located on the supply or return tubes. Plugs provide the electrical probe/console interface for the remote ON/OFF trigger and the temperature measurement. In another aspect, an individual plug or multiple plugs may be utilized. The plugs, or electrical and signal connectors, allow for transmission of signals, data, information to and from the probes to a console computer.

In one embodiment of the smooth probe tip, annealed stainless steel tubing is utilized with an end cap. In another embodiment, the corrugated probe tip is annealed stainless steel tubing with a needle-ore cap. The composition of the tip and tubes, however, can include a variety of metal or plastic materials, as may be compatible with the operational temperatures of the device. A joining tube of similar composition interconnects the components. The probe shaft is about 2 inches to 48 inches in length, and the outer-shell adaptor is about 2 feet to 10 feet, as dependent on the epicardial or endocardial procedures and device application. Aspects of the dimensions may be varied, as well as size, shape and configuration to attain the product that complements the corresponding medical procedure and/or the particular target tissue.

In one aspect, the supply tube 301 is polyimide material sleeved with stainless steel tubing. The supply tube manifold has a sealed distal end, with intermittent holes 315 staggered throughout the probe tip 302 length for even distribution of ice formation along the outer surface 303 of the probe. The number of holes, including the size and dimension of the holes, may vary depending on the desired length and width of the freeze zone. In one embodiment, the approximated hole inner dimensions of 0.012-0.0032 inches was utilized. Any hole size or spacing between holes may be designed, however, to create the desired effects. The holes 315 create a uniform freezing zone as specified for particular procedures. For exemplary purposes only, and not limitation, uniform freezing along a continuous linear path may be desirable to create transmural continuous lesions across a cardiac surface (in the treatment of atrial fibrillation). Hole size, number, and spacing may vary based on probe design and ablation site, including the size ablated and tissue type.

Further, the return tube 306 may be flexible tubing extending up to about 10 feet in length. Again, various sizes and dimensions of the return tube may be utilized according to particular desirable embodiments. In one aspect, the return tube extension is also polyimide tubing with an outer-shell of polyurethane fiber braided tubing encapsulates the internal supply and return tubes into an integral structure, and having a rated burst pressure of about 2000 psi or greater. As burst pressure varies based on materials utilized, the corresponding materials chosen will be capable of withstanding the pressure demanded and utilized by the cryogenic system.

Figure 16:
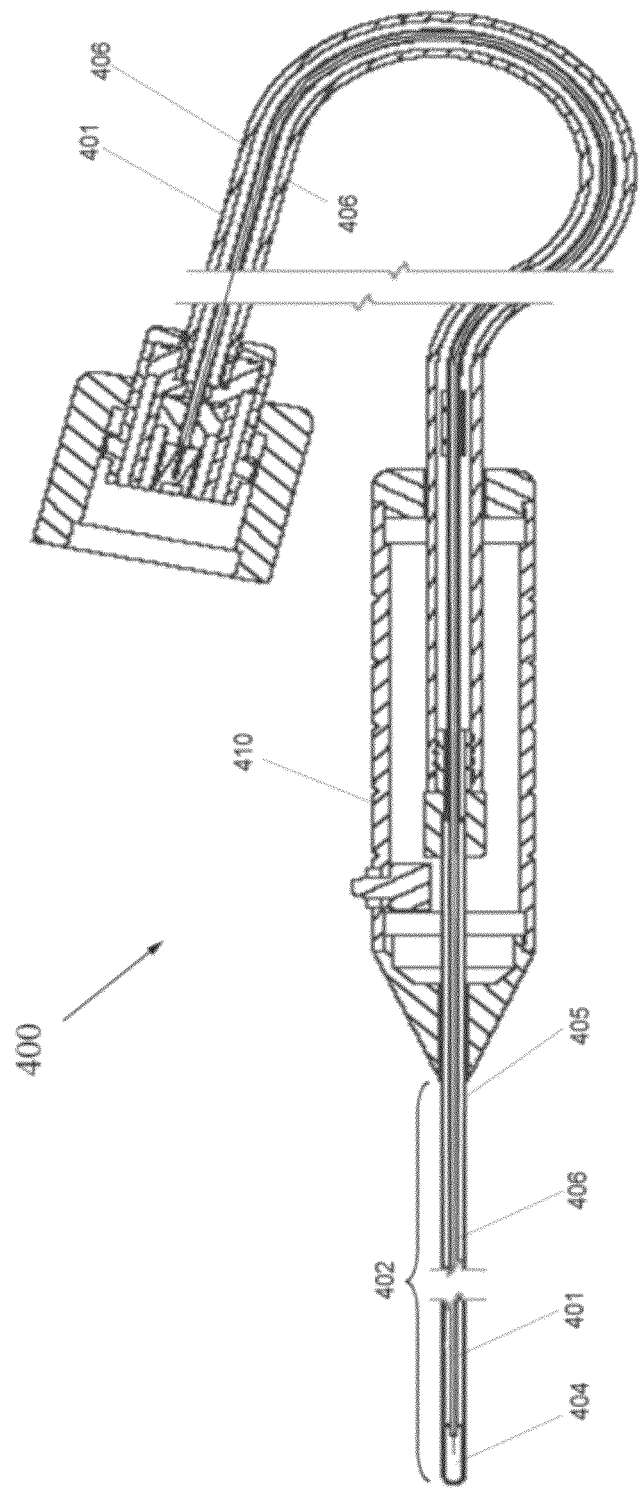
FIG. 16 is an embodiment of the invention including a handle.

Another embodiment of a cryoinstrument 400 is depicted in FIG. 16. The cryoinsrument 400 illustrated here is a cryocatheter 400 having a supply cryoline 401 and a return cryoline 406 coaxially arranged such that the return cryoline 406 surrounds the supply cryoline 401. The flexible catheter 402 utilizes a SCN supercooling system to rapidly cool the distal tip 404 by pushing high pressure SCN through from the proximal end 405 to the distal end 404 of the catheter 402. The internal components accommodate SCN as in the cryoprobe 300 while implementing a flexible catheter tip 402.

The cryocatheter handle 410 allows the user, typically a physician, to easily control the movement of the catheter 402, manually positioning the distal tip 404 or remotely actuating the distal tip 404 movement. In one embodiment, a telescoping catheter 402 can be utilized in order to position the distal tip 404 more accurately. In one aspect, the telescoping feature is integral to the catheter 402. In another aspect, the telescoping feature is a separate component that attaches to the catheter at an interface with the cryolines for secure attachment. Such a telescoping extension extends and retracts as desired before, during or after activation of the freezing protocol. The feature provides precision and control of the catheter, as well as versatility in size, length, and scope of use.

For exemplary purposes only, and not limitation, the telescoping feature is utilized here in a catheter-based system. The feature, however, can be utilized in a rigid or flexible probe or needle tip, or in combination of flexible and rigid components. In one aspect, the telescoping feature is a thaw mechanism which penetrates or encompasses the freeze zone following treatment protocol. Other aspects of telescoping or protrusion-like features may accentuate flexible connections or rigid extensions to control fluid-flow, movement, and accurate positioning of the cryoinstrument.

As with any component of the present system, the parts and components are manufactured with materials conducive to sterilization in the medical setting, and manufactured to withstand extreme temperatures or pressures. In some embodiments, the parts and components of the system have been integrally connected. The parts and connections, however, are removable and may be manufactured to be disposable parts, including the probe, needle, and catheter itself.

The invention facilitates other improvements in cryotherapy, and medical devices or components associated with the treatment. The medical device of the invention allows for the circulation (cooling, delivery, and return) of supercritical cryogen to a cryoprobe for the freezing of targeted tissue. The invention facilitates the eradication of tissue and can thereby decrease hospitalization time; further advantages reduce postoperative morbidities, shorten return to daily functions and work, and further lessen the overall treatment cost. These improvements to device design and application can also increase utilization of the device for the treatment of multiple disease states.

The device of the invention represents an approach in the development of cryosurgical devices by allowing for temperature induced transient vacuum insulation along the shaft of a cryoprobe or catheter; including insulating the shaft of a cryoprobe or catheter and delivery of cryogen in targeted thermal therapy. Furthermore, the device has been developed to couple the temperature initiated vacuum with that of a surface modification along the inner tubes to enable enhanced nucleation and deposition of the saturated gas on the surface of the inner tubes and create an additional layer of insulation. In one aspect, the device of the invention allows for the enhanced deposition on the outer surface of the inner tubes through modification of the tube surface, thereby creating an additional insulation barrier. In another aspect, the saturated gas filled lumen of the outer tube at ambient temperature may be either elevated or at atmospheric pressure.

The embodiments of the present invention may be modified to take the size and shape of any device, container, apparatus, or vessel currently used in industry. As disclosed herein, the cryoinstrument, probe or catheter, in the invention may also be of any size, shape, or dimension. The cryoinstrument may be single use disposable or a multi-use/reusable part (and capable of being sterilized between individual patient treatments). In one embodiment, the longitudinal tubular connections, comprising supply and return lines, extend up to about 6-8 feet or more. Any length, however, may be utilized as designed for particular therapies and treatments. For instance, length can also be achieved by using one or more interconnecting segments. Dimensions less than 12 inches, however, may also be better suited where attached tubing, removable, detachable, or disposable parts are integrated in the design. Specifically, cylindrical or alternative structural designs may be utilized in the cryogenic system for improved catheter/probe access to a tissue target. Further, any rearrangement of the tubes/lines in combination with the components of the above system may take many forms and be of any size, shape, or passageway.

In utilizing the medical device of the present invention, various methods in the industry may be employed in accordance with accepted cryogenic applications. As discussed, the embodiments of the present invention are for exemplary purposes only and not limitation. Advantageously, this device represents an important step in targeted thermal therapies. Various cryosurgical devices and procedures to apply freezing temperatures to a target tissue may be employed for use with the medical device of the present invention. The medical system disclosed herein has been developed to enable and improve some of the approaches used to target or ablate tissue. Furthermore, the medical device can couple controlled pumping of a liquid cryogen through a baffled linear heat exchanger to decrease the overall temperature of the cryogen providing a greater heat capacity of the fluid and thereby resulting in an increased cooling potential in a cryoprobe.

In one embodiment of the system, the mechanical and electrical mechanisms of the operational device are contained within a console, a shell or enclosure that allows the system to be easily transported. The enclosure may then include any mobile feature such as wheels, handles, and fixtures (or allow placement onto a cart having these features) so that the system can be transported to and from the location of treatment. Such mobility allows the system to be easily moved to and from an operating room or site of therapeutic treatment. It is also noted that the system is readily separable from the cryogen fill tanks and fill lines that initially supply the system with the liquid nitrogen or other such cryogenic fluid at the supply port 29 (As shown in FIG. 1). This improved feature eliminates the bulkiness of standard cryogenic medical devices.

As stated prior, the system may be operated while it is in direct connection to the bulk cryogen supply, or as deemed obvious by current supply systems in the art.

As presented, the multiple embodiments of the present invention offer several improvements over standard medical devices currently used in cryogenic industry. The improved cryogenic medical system remarkably enhances its utilization for the cooling, delivery and return of a liquid cryogen to a cryoprobe or cryocatheter for the freezing of targeted tissue. The invention provides cost savings and significantly reduced treatment times which further reduce expenditures in the healthcare setting. The previously unforeseen benefits have been realized and conveniently offer advantages for the treatment of multiple disease states. In addition, the improvements enable construction of the device as designed to enable easy handling, storage, and accessibility.

As exemplified, the device may include any unitary structure, vessel, device or flask with the capacity to integrally incorporate any combination of such structures. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

In addressing the treatment of cardiac arrhythmias, various studies have been conducted to treat cardiac tissue in mammals. Particularly, studies have been conducted on canines to verify and confirm the novelty of the present invention.

Prior to an epicardial procedure, the probes are selected—one corrugated tip cryoprobe and one smooth tip cryoprobe to be placed at the target tissue site. The probes are sterilized and withstand various sterilization temperatures and treatments.

For exemplary purposes only, and not limitation, the following study was conducted based on current freezes used in medical procedures, freezes performed on each heart for 60 sec, 90 sec, or 120 sec depending on their location. As noted by the surgeon, and indicated by external thermocouples, each freeze created transmural cryolesions that could be visualized after freezing for about 15 to 30 seconds. A cryoclamp was integrated with a centering piece to support the cryoprobe. The corrugated cryoprobe was inserted through the entire clamp and successfully placed at the desired epicardial locations. The annealed smooth tip of the cryoprobe was pre-shaped prior to a 90° angle using a manual tube bender. The bent tip was then inserted through an opening at the clamp jaw site and shaped by hand to match the profile of the jaws. Although the smooth tip was less flexible (annealed tubing versus corrugated annealed tubing), the cryoprobe was able to be placed as specified in the protocol. The smooth tip cryoprobe inserts into the endocardial space more easily as compared to the corrugated-tip probe due to the tip surface configuration.

Performance comparisons between the corrugated and smooth tip probe configurations were conducted with internal and external temperature monitoring demonstrating similar freeze performance. In the ventricle freeze model, the smooth tip appears to create a more defined and precise linear freeze lesion (less lateral spread with damage more focused near the probe).

Interconnecting parts presents additional challenges. In one embodiment, a cryogenic coaxial connector design proved successful with no leaks occurring at the probe or console interfaces. The elastic and/or flexible nature of the hose assembly and/or tubing can be integrated with the various connected parts and interconnections. For exemplary purposes, and not limitation, the cryoablation system's placement in reference to the sterile surgical field will determine the segmentation of interconnecting parts and components (e.g. umbilical tubing ranging from about 6 feet to 8 feet in length, more or less depending on positioning and location of the ablation site).

All freezes were initiated with a pressure above 1000 psi, a single freeze being conducted per charge of the internal pressurization chamber (Note: "Charge" here is intended to refer to the fill and pressurization of the cryogen in the pressurization chamber.) Automated and electronic computer controls can assist in achieving a desired fill cycle.

Immediately following the fill cycle, vent valves were closed, the pressure valve opened, and the internal pressurization heaters were activated. Although pressurization times varied, the system was pressurized to 1000 psi within 150 seconds for all runs. The pressurization cycle was accelerated by closing the pressure valve upon completion of the freeze cycle maintaining the residual pressure in the pressure cylinder following each run (at about 500 psi). Heating of the pressure cylinder maintains the temperature at about 25-35° C. to further aid the pressurization cycle, keeping SCN pressures between about 500 psi to about 1000 psi for greater efficiency. The pressure around about 1000 psi may fluctuate slightly to treat target tissue sites within about 15 seconds to about 120 seconds (about 2 minute timeframes for treatment).

Upon placement of the cryoprobe, the injection valve was activated (opened) to commence cryogen flow. The cryoprobes' internal thermocouples showed a rapid and precipitous drop in temperature to around −170° C. in less than 5 sec regardless of the probe tip (smooth or corrugated) utilized and despite the locus of the freeze site (e.g. in the clamp, on the surface, or endocardially through a purse string suture). In one aspect, a narrower freeze zone may be achieved by utilizing a smooth tip probe. The narrower freeze zone creates defined lesion sites, including linear lesions, and further prevents collateral damage. Current linear lesions can be created in the range of about 2 cm-5 cm or greater.

Accordingly, the benefits of utilizing liquid nitrogen, specifically SCN, surpass the reduced pressure systems in operation today (e.g. nitrous oxide and argon based systems). The heat extraction by SCN exceeds that of the other devices, allowing for quicker treatment procedures and overall reduced treatment times. Further, the interconnected instruments can be miniaturized and adjusted to accommodate various medical procedures.

After freezing for the desired time, the injection valve was closed, stopping the cryogen flow, and warm saline was utilized to rapidly thaw the probe. Immediately following the closure of the injection valve (end of freeze), the pressurization heaters were turned off, the pressure valve closed, and the high pressure vent valve opened. When the system is returned to atmospheric pressure (a relative pressure of 0 psi), the device is again ready to repeat the process. In another embodiment, the probes are rapidly thawed by activation of the integrated thaw cycle feature of the device.

The connector may include a threaded turn valve, snap or twist quick connect, ¼ turn snap-fit valve, a snap-fit seal, or other types of connectors that integrate the internal components of the probe with that of the cryoassembly. Such a component has internal and external mating features to provide a leak-proof seal.

For exemplary purposes, and not limitation, the 2 min endocardial freezes recorded a temperature of −100° C. on the exterior surface of the atrium within 60 seconds. No detrimental effects to the animal or to the tissue were observed in this "overfreeze" scenario despite freeze durations at least double what were utilized to ablate the tissue In safety terms, this evidence realizes the safety design of the cryoengine.

Furthermore, in other embodiments of the system, the thermal performance of the probes was as expected. Average return flow temperatures of −170.5±2.8° C. were recorded. A noticeable difference between the average tank pressure decay for the smooth tip versus corrugated tip probe was observed. No apparent performance differences, however, were noted when comparing smooth versus corrugated tip probes.

Endocardial Procedure

In one embodiment, a canine model was utilized for an endocardial catheter cryoablation of the right atria via the inferior vena cava. The catheter, however, may be introduced via any blood vessel leading to the heart. After sedation and proper venous lines in place, the femoral veins and jugular veins were cannulised to permit access for catheters; a femoral artery access was also implemented to determine if any deviations in hemodynamic values occur during the procedure. Through the percutaneous accesses, multipolar reference catheters were placed at each of the following loci: 1) in the coronary sinus, 2) at the right atrial free wall, 3) at the His bundle, 4) at the cavo-tricuspid isthmus, and 5) for 3D mapping of the right atrium with a visualization system such as fluoroscopic visualization guidance techniques.

Conduction was tested, clockwise and counterclockwise, in the cavo-tricuspid isthmus. Application of cryothermal energy was applied to each of these areas.

While pacing the coronary sinus, cryothermal energy was applied. An isthmus block was achieved (to generate a cavo-tricuspid isthmic block) with a single application by titrating the cryothermal energy to progressively lower temperatures during pacing. After performing the bidirectional block, the pacing site switches to the distal electrode of the catheter to the right atrial free wall to re-assess conduction via the cavo-tricuspid isthmus while pacing at the same cycle length. A visualization system was then utilized to map the right atrium post ablation. A trans-septal puncture was performed by inserting a needle through a sheath to perforate the septum between the right and left atrium permitting the entry of the cryoablation catheter to the left atrium. Ablations were then performed in the left atrium to achieve a block using a time and specified power protocol.

Epicardial Procedure

A protocol for one embodiment of the epicardial procedure is as follows:

The purpose of this study is to evaluate new cryo-ablation technologies using a standard 10 cm cryoprobe as a control. This small sample study evaluates general safety and effectiveness to achieve transmural lesions in a beating heart canine model at six target locations. A cryoclamp is used in combination with the probes to create lesions at the left atrial appendage (LAA), right atrial appendage (RAA), Right Pulmonary Veins (RPV), and Left Pulmonary Veins (LPV). The probes are used alone to create two right ventricular epicardial lesions and one right atrial endocardial lesion. The cryoprobe freezes the target tissue and blocks the electrical conduction pathway. A cryoclamp is used to encircle the pulmonary veins and freeze the tissue to block the electrical conduction pathway. Used alone, the cryoprobe creates linear lesions.

In an embodiment of the present invention, one probe uses a corrugated bellow segment in the distal tip. Another embodiment utilizes a probe with a flexible 10 cm long, 3.2 mm diameter, ablation segment. At times of 90 and 120 seconds, respectively, and after complete visual transmural fronts, opposite-side tissue temperatures are recorded for the atrial appendages and pulmonary veins, respectively. Right ventricular epicardial lesion depth (histological assessment after 7-10 days) is achieved with 60 and 120 second freeze duration (more often, however, the freeze achieves its expected treatment performance in the range of 15-30 seconds). The same is recorded for a right atrial endocardial lesion. An overview of the test protocol for the current technology is presented in Table 1.

TABLE 1

Lesions and Ablation Duration.

| Lesions | With Clamp (Y/N) | Purpose of Lesion | Freeze Duration (s) |
|---|---|---|---|
| RPV | Y | Time to complete visual transmural frost. Opposite-side temperature curve (1 or 2 points). | 120 |
| LPV | Y | Time to complete visual transmural frost. Opposite-side temperature curve (1 or 2 points). | 120 |
| LAA | Y | Time to complete visual transmural frost. Opposite-side temperature curve (1 or 2 points). | 90 |
| RAA | Y | Time to complete visual transmural frost. Opposite-side temperature curve (1 or 2 points) | 90 |

TABLE 1-continued

Lesions and Ablation Duration.

| Lesions | With Clamp (Y/N) | Purpose of Lesion | Freeze Duration (s) |
|---|---|---|---|
| 2 linear right ventricular lesions | N | Lesion depth for a given freeze duration. | 60<br>120 |
| Right atrial endocardial lesion through purse string | N | Time to complete visual transmural frost. Opposite-side temperature curve (1 or 2 points) | 120 or until frost is visible and linear (max 180) |

In one aspect of epicardial ablation, a median sternotomy is first performed. A chest retractor is placed in this space and opened to expose the organs and vessels of the thoracic cavity. The left internal mammary artery for arterial pressure monitoring is cannulated. The pericardium is opened to create a pericardial cradle. Circumferentially, the right and left pulmonary veins are divided out.

During the ablation procedure presented, a cryoprobe in combination with a cryoclamp is utilized to ablate the atrial appendages and pulmonary veins according to the durations listed in Table 1. Temperatures of each lesion are measured using the thermocouples attached to the opposite tissue surface. The time to complete visual frost and the opposite side tissue temperature for each lesion were recorded. Then, the probe was utilized independently to create 2 linear right ventricular epicardial lesions, as well as 1 right atrial endocardial lesion using a purse-string access (as per Table 1).

Following ablation, the probe was thawed with warm saline solution and removed. The pericardium was loosely reapproximated as well as the sternum, followed by closing the muscle and skin via sutures.

A number of implementations have been described. Nevertheless, it will be understood that various modifications may be made without departing from the spirit and scope of this document. In particular, for example, cryogenic systems and probes/catheters are described as employing SCN as the cryogen, but non-critical liquid nitrogen may also be utilized, or other cryogens (as may be integrated in a modified design). Moreover, cryoprobes and cryocatheters can be employed to deliver targeted cryotherapy to regions of a patient's body other than the patient's heart (including, for example, a patient's prostate gland, or other glands; a portion of the patient's gastro-intestinal tract; a small (e.g. varicose) vein; or other suitable internal treatment sites and tissues). Multiple cooling and thermally insulating regions can be provided, and the regions can be formed in various shapes and sizes. Accordingly, other implementations are within the scope of the following claims.

Further, the studies described utilize a single cryoprobe or catheter. The use of multiple cryoprobes and catheters, alone or in combination, or simultaneously, can facilitate the performance of hybrid or dual epicardial and endocardial ablation procedures. The cryoablation process utilizing the various described technologies can be performed utilizing cardiac bypass or in off bypass beating hearts (as in the above described protocols). The ability to perform the procedure off bypass offers tremendous novelty to the cryodevice since no current cryoabaltion technology can achieve the effective ablation in the timeframe of less than about three minutes (3 minutes per lesion in a beating heart). In addition, the ablation process can be achieved via open sternotomy procedures, minimally invasive thoroscopic procedures, percutaneously or through vascular access. Further, the cryoablation procedure can also be performed in combination with other ablation or surgical treatment modalities, including radiofrequency, HiFu, laser or surgical incision among others representing various approaches to the above referenced hybrid procedure.

What is claimed is:

1. A cryogenic medical system for use in patient treatment procedures, said cryogenic system comprising:

at least one cryoengine including a dewar containing a cryogen, a flow generator within said dewar; at least one pressurization system having one or more heaters arranged therein, at least one port, one or more control valves, a first vessel and a second vessel interconnected, wherein said first vessel is submersed in said cryogen and has a first temperature and said second vessel is positioned outside said cryogen and has a second temperature greater than said first temperature; at least a first attachment connecting said flow generator to said port of said pressurization system, and one or more cryolines connected to said port; and one or more cryoinstruments comprising one or more tubular structures arranged therein, said cryoinstruments each having a proximal end which connects with said cryolines of said cryoengine and a distal end positioned at a treatment site;

wherein said pressurization system produces supercritical cryogen, pressurized cryogen, or one or more pseudo-fluids, alone or in combination.

2. The cryogenic medical system of claim 1, wherein said cryolines comprise at least a supply tubing connecting said cryoengine to said cryoinstrument and supplying said supercritical cryogen to said one or more tubular structures; and at least a return tubing to return said cryogen to said dewar.

3. The cryogenic medical system of claim 1, wherein said one or more tubular structures comprise at least a first tubing and a second tubing are positioned in a coaxial or side-by-side configuration.

4. The cryogenic medical system of claim 3, wherein said first tubing and second tubing are positioned with a flexible tubular shaft.

5. The cryogenic medical system of claim 1, wherein said pressurization system provides continuous flow of said supercritical cryogen.

6. The cryogenic medical system of claim 1, wherein said treatment site is a mammalian cardiac tissue.

7. The cryogenic medical system of claim 6, wherein said mammalian cardiac tissue freezes within about 10 seconds to about 180 seconds.

8. The cryogenic medical system of claim 1, wherein said cryoinstrument is an epicardial cryogenic probe or an endocardial cryogenic catheter.

9. The cryogenic medical system of claim 1, wherein said treatment site freezes by way of formation of an iceball in a diameter of about 2 mm to 30 mm or greater with a length of 1 mm to 130 mm or greater and within about 10 seconds to 180 seconds.

10. The cryogenic medical system of claim 9, further comprising a plurality of said treatment sites.

11. The cryogenic medical system of claim 9, wherein said cryoinstrument is released from said treatment site by a thawing mechanism used in combination with said cryoinstrument.

12. The cryogenic medical system of claim 11, wherein said thawing mechanism is integral to said cryoinstrument, said thawing mechanism capable of extending and retracting.

13. The cryogenic medical system of claim 1, further comprising one or more connectors that interconnect said cryolines of said cryoengine and said tubular structures of said cryoinstruments.

14. The cryogenic medical system of claim 13, wherein said one or more connectors reversibly attach with and detach from said cryoengine or said cryoinstruments.

15. The cryogenic medical system of claim 13, wherein said one or more connectors have a telescoping feature, snap-on, twist-on or quick-connect feature providing easy attachment.

16. The cryogenic medical system of claim 15, wherein said telescoping feature extends and retracts to flexibly position said cryolines and said tubular structures.

17. The cryogenic medical system of claim 1, wherein said cryoinstrument comprises a handle which maneuvers said distal end to said treatment site.

18. The cryogenic medical system of claim 17, wherein said handle comprises one or more displays which monitor sensors and communicate information for operation of said cryoengine and said cryoprobes.

19. The cryogenic medical system of claim 1, wherein said cryoinstrument comprises a telescoping feature which extends and retracts during a treatment procedure.

20. The cryogenic medical system of claim 1, wherein said supply tubing is interconnected with said return tubing to form an integral cryotube and provide controlled rapid delivery of said supercritical cryogen to and from said distal end of said cryoinstrument.

21. The cryogenic medical system of claim 20, wherein said integral cryotube is flexible.

22. The cryogenic medical system of claim 1, wherein said cryoengine is a multi-port system wherein one or more of said pressurization systems include one or more manifolds to perform multiple treatment procedures.

23. The cryogenic medical system of claim 22, wherein said pressurization systems and said manifolds are configured to perform said multiple treatment procedures simultaneously or sequentially.

24. The cryogenic medical system of claim 23, wherein said multiple treatment procedures include one or more epicardial treatments, one or more endocardial treatments, individually or in any combination thereof.

25. The cryogenic medical system of claim 1, wherein said cryoinstruments include a component that attach to said treatment site, wherein said treatment site is a mammalian cardiac tissue.

26. The cryogenic medical system of claim 1, further comprising a monitoring system for visualizing placement of said distal end of said cryoinstrument through to said treatment site.

27. The cryogenic medical system of claim 26, wherein said monitoring system is internal to said cryoinstrument and includes fiber optic visualization.

28. The cryogenic medical system of claim 1, wherein said cryoengine and said cryoinstrument comprise sensors to monitor conditions including temperature, pressure, leakage, flow rate, cardiac electrical activity, freeze zone formation, computer simulated cryoinstrument configuration, and placement of said cryoinstrument.

29. The cryogenic medical system of claim 1, wherein said cryoengine and said cryoinstrument has remote controls.

30. The cryogenic medical system of claim 29, wherein said remote controls regulate treatment protocols, including treatment times, iceball formation, probe placement, probe angle, probe deflection, temperature and pressure.

31. The cryogenic medical system of claim 29, further comprising a warming feature to maintain a determined size of said iceball formation, control treatment times, and allow for probe detachment, tissue thawing, and heating.

32. The cryogenic medical system of claim 1, wherein said cryoinstrument creates a transmural linear lesion.

33. A method of performing cryotherapy on cardiac tissue using said cryogenic medical system of claim 1, comprising:
    filling said pressurized system with said cryogen;
    activating said pressurized system to form a pressurized supercritical cryogen; and
    directing said pressurized cryogen through one or more supply lines to said cryoinstruments and from said cryoinstruments through said one or more return lines.

34. The method of claim 33, wherein said step of directing includes a step of cryoablating said cardiac tissue.

35. The method of claim 34, wherein said step of cryoablating said cryoinstruments create transmural lesions.

36. The method of claim 34, wherein said cryoinstruments utilize flexible interconnections to provide epicardial treatment upon a surface of a mammalian heart or to provide endocardial treatment by way of vessel access or cavity access through to an interior surface of the heart.

37. The method of claim 36, further comprising a step of utilizing hybrid ablation procedures, simultaneously or in tandem, to ablate tissue in any region of said mammalian heart or within vasculature in a mammalian body, alone or in combination with said epicardial treatments and said endocardial treatments.

38. The method of claim 37, wherein said hybrid ablation procedures comprise cryoablation in combination with surgical intervention or one or more ablative energy sources including radiofrequency, HiFu, and laser therapy.

39. A cryo-apparatus for performing cryoablation in a mammalian heart, said cryo-apparatus comprising:
    one or more cryoinstruments interconnected with a first cryoline and a second cryoline to form a unitary tubular structure which circulates a cryogenic medium to and from said one or more cryoinstruments;
    a container having a cryogenic medium contained therein;
    a heat exchanger surrounded by a subcooling chamber;
    at least one pressurized apparatus having one or more heaters arranged therein, at least one port, and one or more control valves, wherein at least a first portion of said pressurized apparatus is inside said cryogenic medium and at least a second portion of said pressurized apparatus is outside said cryogenic medium;

a flow generator which delivers said cryogenic medium to said port of said pressurized apparatus, said control valves releasing said cryogenic medium in a supercritical state from said port to said heat exchanger, and through to said one or more cryoinstruments at a target site of cardiac tissue.

40. The cryo-apparatus of claim 39, wherein said cryogenic medium is liquid nitrogen.

* * * * *